(12) United States Patent
Nemet et al.

(10) Patent No.: US 11,141,176 B2
(45) Date of Patent: Oct. 12, 2021

(54) TOOLS AND METHODS FOR DACRYOCYSTORHINOSTOMY

(71) Applicant: TEARFLOW CARE LTD., Haifa (IL)

(72) Inventors: Arie Nemet, Givat Shmuel (IL); Idan Tobis, Beth Hashmonai (IL)

(73) Assignee: TEARFLOW CARE LTD.

( * ) Notice: Subject to any disclaimer, the term of this patent is extended or adjusted under 35 U.S.C. 154(b) by 0 days.

(21) Appl. No.: 16/650,936

(22) PCT Filed: Aug. 27, 2018

(86) PCT No.: PCT/IL2018/050943
§ 371 (c)(1),
(2) Date: Mar. 26, 2020

(87) PCT Pub. No.: WO2019/064292
PCT Pub. Date: Apr. 4, 2019

(65) Prior Publication Data
US 2020/0246028 A1 Aug. 6, 2020

Related U.S. Application Data

(60) Provisional application No. 62/563,812, filed on Sep. 27, 2017.

(51) Int. Cl.
*A61B 17/17* (2006.01)
*A61B 17/16* (2006.01)
*A61F 9/007* (2006.01)

(52) U.S. Cl.
CPC ...... *A61B 17/1785* (2016.11); *A61B 17/1688* (2013.01); *A61F 9/00772* (2013.01); *A61B 17/1764* (2013.01)

(58) Field of Classification Search
CPC .......... A61B 17/1764; A61B 17/1785
See application file for complete search history.

(56) References Cited

U.S. PATENT DOCUMENTS 4,920,958 A * 5/1990 Walt ............... A61B 17/1714
606/103
5,112,337 A * 5/1992 Paulos ............. A61B 17/1764
606/96

(Continued)

FOREIGN PATENT DOCUMENTS

| GB | 484499 | 5/1938 |
| WO | 03007861 | 1/2003 |

OTHER PUBLICATIONS

International Search Report, International Application No. PCT/IL2018/050943, dated Jan. 3, 2019.

*Primary Examiner* — Nicholas W Woodall
(74) *Attorney, Agent, or Firm* — The Roy Gross Law Firm, LLC; Roy Gross

(57) ABSTRACT

A dacryocystorhinostomy (DCR) tool (10) includes a perforating shaft (30) having a distal perforating tip (32) configured to form a bypass between a lacrimal sac and a nasal cavity through a lateral side of the lacrimal sac, a lacrimal bone, and nasal mucosa. A DCR guide (20) includes a nasal guide component (40) configured to be inserted into the nasal cavity and having a distal guide tip (42); and a lacrimal guide component (50) shaped so as to define a guide channel (52) that orients the DCR guide (20) with respect to the distal perforating tip (32) during advancing of the distal perforating tip (32) through a lacrimal passageway and into the lacrimal sac, until contact of the distal perforating tip (32) with the distal guide tip (42) blocks further advancing of the distal perforating tip (32). The DCR guide (20) constrains the distal guide tip (42) to fall in a path of advancement of the distal perforating tip (32). Other embodiments are also described.

19 Claims, 16 Drawing Sheets

(56) References Cited

U.S. PATENT DOCUMENTS

| | | | | |
|---|---|---|---|---|
| 5,163,940 A | * | 11/1992 | Bourque | A61B 17/1714 606/103 |
| 5,562,664 A | * | 10/1996 | Durlacher | A61B 17/1714 606/103 |
| 5,613,971 A | * | 3/1997 | Lower | A61B 17/1714 606/102 |
| 6,342,056 B1 | * | 1/2002 | Mac-Thiong | A61B 17/1757 606/103 |
| 7,201,756 B2 | * | 4/2007 | Ross | A61B 17/1714 606/96 |
| 2003/0216742 A1 | * | 11/2003 | Wetzler | A61B 17/17 606/96 |
| 2011/0282350 A1 | | 11/2011 | Kowarsch et al. | |
| 2017/0252048 A1 | | 9/2017 | Sauer et al. | |

* cited by examiner

TOOLS AND METHODS FOR DACRYOCYSTORHINOSTOMY

CROSS-REFERENCE TO RELATED APPLICATIONS

The application is a National Phase of PCT Patent Application No. PCT/IL2018/050943 having International filing date of Aug. 27, 2018, which claims the benefit of priority of U.S. Provisional Patent Application No. 62/563,812, filed Sep. 27, 2017. The contents of the above applications are all incorporated by reference as if fully set forth herein in their entirety.

FIELD OF THE APPLICATION

The present invention relates generally to surgical eye procedures, and specifically to tools and methods for performing dacryocystorhinostomy.

BACKGROUND OF THE APPLICATION

Blockage of the nasolacrimal (tear) duct in adults results in excessive tearing (epiphora), which causes suffering, a substantial disruption to the patient's ability to function, and a substantial reduction in quality of life. Blockage can cause severe infections of the nasolacrimal ducts and the eye socket, and danger to the eye.

Dacryocystorhinostomy (DCR) is a surgical procedure for restoring the flow of tears into the nose from the lacrimal sac when the nasolacrimal duct is blocked, by opening the blockage and forming a bypass for drainage toward the nose. An external approach to DCR was developed in 1904 and includes cutting skin, muscle, bone, and nasal mucosa and bypass formation. DCR can also be performed endoscopically through the nose, to form a bypass between the nasolacrimal duct and the nose. It is estimated that about 40% of the DCR surgeries are performed using the endoscopic method and about 60% using the external approach. The two operations are similarly complicated and require special training. This surgery may be performed by specialists in oculoplasty or otorhinolaryngology, but surgery is often performed by a team of two specials from both fields. In general, DCR is a complex surgery that is usually performed under general anesthesia or deep blur, and which may involve scars and discomfort. DCR success rates are generally 75-90%. Therefore, many patients and surgeons prefer to avoid treating epiphora, and patients continue to suffer.

SUMMARY OF THE APPLICATION

Embodiments of the present invention provide dacryocystorhinostomy (DCR) tools and methods for performing dacryocystorhinostomy. The DCR tools comprise a DCR guide and, for some applications, a perforating shaft having a distal perforating tip configured to form a bypass between a lacrimal sac and a nasal cavity through a lateral side of the lacrimal sac, a lacrimal bone, and nasal mucosa.

The DCR guide comprises a nasal guide component and a lacrimal guide component. The nasal guide component is configured to be inserted into the nasal cavity and has a distal guide tip. The lacrimal guide component is shaped so as to define a guide channel that is configured to orient the DCR guide (via the lacrimal guide component) with respect to guide the distal perforating tip of the perforating shaft during advancing of the distal perforating tip through a lacrimal passageway and into a lacrimal sac, until contact of the distal perforating tip with the distal guide tip of the nasal guide component blocks further advancing of the distal perforating tip.

The DCR guide is configured to constrain the distal guide tip of the nasal guide component to fall in a path of advancement of the distal perforating tip. The lacrimal passageway to a large extent sets the path of advancement of the distal perforating tip, which in turn sets an orientation and location of the perforating shaft. The perforating shaft in turn sets an orientation and location of the lacrimal guide component, which sets an orientation and location of the nasal guide component, including the distal guide tip, in the nasal cavity. As a result, the distal guide tip is automatically and non-electrically positioned in the path of advancement of the distal perforating tip, and thus comes in contact with the distal perforating tip and blocks its advancement.

For some applications, the nasal guide component, including the distal guide tip, is shaped so as to define a nasal guidewire-accepting channel. Typically, a distal opening of the nasal guidewire-accepting channel faces at least partially in a lateral direction that faces toward the lacrimal guide component.

For some applications, the DCR tool further comprises, in addition to the perforating shaft, a lacrimal guidewire shaft having a distal tip. In these applications, the perforating shaft is typically solid, i.e., does not define a channel therethrough. The lacrimal guidewire shaft, including the distal tip thereof, is shaped so as to define a lacrimal guidewire-accepting channel. The guide channel of the lacrimal guide component is configured to orient the DCR guide (via the lacrimal guide component) with respect to the distal tip of the lacrimal guidewire shaft during advancing of the distal tip of the lacrimal guidewire shaft through the guide channel and the lacrimal passageway and into the lacrimal sac. The DCR guide is configured to constrain the distal guide tip of the nasal guide component to fall in a path of advancement of the distal tip of the lacrimal guidewire shaft.

For other applications, the perforating shaft, including the distal perforating tip, is shaped so as to define the lacrimal guidewire-accepting channel.

For some applications, a method of performing DCR is provided. The method does not require making an incision through skin, since access to the bypass is provided directly through the natural lacrimal punctum and canaliculi. The nasal guide component of the DCR guide is inserted into a nasal cavity of a patient's body. The nasal guide component need not be inserted precisely by the surgeon, so long as it is inserted into the correct nostril, because it will be precisely oriented and positioned by the DCR guide, as described hereinbelow. The perforating shaft is advanced through the guide channel of the lacrimal guide component of the DCR guide and a lacrimal passageway and into a lacrimal sac. The lacrimal passageway includes a lacrimal punctum (either inferior or superior), a lacrimal canal (either inferior or superior), and a common canaliculus. Surgeons skilled in the DCR art generally are able to advance the perforating shaft through the lacrimal passageway without difficulty.

The DCR guide constrains the distal guide tip of the nasal guide component to fall in a path of advancement of the distal perforating tip. As a result of this constraint, the DCR guide typically positions the distal guide tip of the nasal guide component at an axilla of a middle turbinate of the nasal cavity. A bypass is formed between the lacrimal sac and the nasal cavity by advancing the distal perforating tip of the perforating shaft through a lateral side of the lacrimal sac, a lacrimal bone, and nasal mucosa, until contact of the distal perforating tip with the distal guide tip of the nasal guide component blocks further advancing of the distal perforating tip. This contact prevents over-advancement the distal perforating tip, which might otherwise perforate tissue across the nasal cavity, which is generally no more than several millimeters beyond the bypass.

For some applications, a guidewire is placed such that the guidewire passes through the lacrimal passageway, the bypass, and at least a portion of the nasal guidewire-accepting channel. Typically, the guidewire is placed such that the guidewire passes through the lacrimal passageway, the bypass, the entire the nasal guidewire-accepting channel, and out of a proximal end of the nasal guidewire-accepting channel. Typically, the distal opening of the nasal guidewire-accepting channel faces at least partially in the above-mentioned lateral direction that faces toward the lacrimal guide component.

For some applications, a dilator is advanced along and over the guidewire and through the lacrimal passageway and into the bypass, and the bypass is dilated using the dilator. For some applications, a tubular support element is advanced along and over the guidewire and through the lacrimal passageway and into the bypass, and the guidewire is removed from the patient's body while leaving the tubular support element in place in the bypass.

There is therefore provided, in accordance with an application of the present invention, a method of performing dacryocystorhinostomy (DCR), the method including:

inserting a nasal guide component of a dacryocystorhinostomy (DCR) guide into a nasal cavity of a patient's body;

advancing a perforating shaft through a guide channel of a lacrimal guide component of the DCR guide and a lacrimal passageway and into a lacrimal sac, the lacrimal passageway including a lacrimal punctum, a lacrimal canal, and a common canaliculus; and forming a bypass between the lacrimal sac and the nasal cavity by advancing a distal perforating tip of the perforating shaft through a lateral side of the lacrimal sac, a lacrimal bone, and nasal mucosa, until contact of the distal perforating tip with a distal guide tip of the nasal guide component blocks further advancing of the distal perforating tip, wherein the DCR guide constrains the distal guide tip of the nasal guide component to fall in a path of advancement of the distal perforating tip.

For some applications, inserting the nasal guide component and the lacrimal guide component includes using the DCR guide to set a desired angle between respective central longitudinal axes of the nasal guide component and the perforating shaft. For some applications, setting the desired angle includes using an arcuate portion of the DCR guide that allows relative movement between the nasal guide component and the lacrimal guide component to set the desired angle.

For any of the applications described hereinabove, the nasal guide component, including the distal guide tip, may be shaped so as to define a nasal guidewire-accepting channel, and the method may further include, after forming the bypass, placing a guidewire such that the guidewire passes through the lacrimal passageway, the bypass, and at least a portion of the nasal guidewire-accepting channel. For some applications, placing the guidewire includes placing the guidewire such that the guidewire passes through the lacrimal passageway, the bypass, the entire nasal guidewire-accepting channel, and out of a proximal end of the nasal guidewire-accepting channel. For some applications, a distal opening of the nasal guidewire-accepting channel faces at least partially in a lateral direction that faces toward the lacrimal guide component. For some applications, the nasal guide component includes (a) an outer guide element that is shaped so as to define a nasal-shaft-accepting channel therethrough, and (b) a nasal shaft that is slidable through the nasal-shaft-accepting channel, and the nasal shaft is shaped so as to define the distal guide tip and the nasal guidewire-accepting channel; the method further includes coupling together the outer guide element and the nasal shaft by sliding the nasal shaft through the nasal-shaft-accepting channel; and when the outer guide element and the nasal shaft are coupled together, a distal opening of the nasal guidewire-accepting channel is constrained by the outer guide element and the nasal shaft to face at least partially in a lateral direction that faces toward the lacrimal guide component. For some applications, coupling together the outer guide element and the nasal shaft further includes locking the nasal shaft rotationally with respect to the nasal-shaft-accepting channel, thereby maintaining the distal opening of the nasal guidewire-accepting channel facing at least partially in the lateral direction.

For some applications, the perforating shaft, including the distal perforating tip, is shaped so as to define a lacrimal guidewire-accepting channel, and placing the guidewire such that the guidewire passes through the lacrimal passageway includes advancing the guidewire through the lacrimal guidewire-accepting channel while the perforating shaft is disposed passing through the lacrimal passageway. For some applications, placing the guidewire such that the guidewire passes through the lacrimal passageway, the bypass, and the nasal guidewire-accepting channel includes advancing the guidewire through the lacrimal guidewire-accepting channel while (a) the perforating shaft is disposed passing through the lacrimal passageway and the bypass, and (b) the distal perforating tip is in contact with the distal guide tip of the nasal guide component.

For some applications, placing the guidewire such that the guidewire passes through the lacrimal passageway includes: removing the perforating shaft from the patient's body; inserting a lacrimal guidewire shaft through the guide channel of the lacrimal guide component and the lacrimal passageway and into the lacrimal sac, wherein the lacrimal guidewire shaft, including a distal tip thereof, is shaped so as to define a lacrimal guidewire-accepting channel, and wherein the DCR guide constrains the distal guide tip of the nasal guide component to fall in a path of advancement of the distal tip of the lacrimal guidewire shaft; and advancing the guidewire through the lacrimal guidewire-accepting channel while the lacrimal guidewire shaft is disposed passing through the lacrimal passageway. For some applications, placing the guidewire such that the guidewire passes through the lacrimal passageway, the bypass, and the nasal guidewire-accepting channel includes advancing the guidewire through the lacrimal guidewire-accepting channel while (a) the lacrimal guidewire shaft is disposed passing through the lacrimal passageway and the bypass, and (b) the distal tip of the lacrimal guidewire shaft is in contact with the distal guide tip of the nasal guide component.

For some applications, placing the guidewire includes placing the guidewire such that a first end of the guidewire extends out of the patient's body through the lacrimal punctum and a second end of the guidewire, opposite the first end, extends out of the patient's body through the nasal cavity.

For some applications, the method further includes, after placing the guidewire: advancing a dilator along and over the guidewire and through the lacrimal passageway and into the bypass; and dilating the bypass using the dilator. For some applications, the dilator includes an inflatable element, and dilating the bypass includes inflating the inflatable element in the bypass. For some applications, the method further includes, after dilating the bypass: advancing a tubular support element along and over the guidewire and through the lacrimal passageway and into the bypass; and removing the guidewire from the patient's body while leaving the tubular support element in place in the bypass.

For some applications:
the nasal guide component includes (a) an outer guide element that is shaped so as to define a nasal-shaft-accepting channel therethrough, and (b) a nasal shaft that is slidable through the nasal-shaft-accepting channel, and the nasal shaft is shaped so as to define the distal guide tip, and the method further includes coupling together the outer guide element and the nasal shaft by sliding the nasal shaft through the nasal-shaft-accepting channel.

For some applications, advancing the distal perforating tip includes drilling the distal perforating tip through the lateral side of the lacrimal sac, the lacrimal bone, and the nasal mucosa.

For some applications, advancing the distal perforating tip includes punching the distal perforating tip through the lateral side of the lacrimal sac, the lacrimal bone, and the nasal mucosa.

There is further provided, in accordance with an application of the present invention, a method of performing dacryocystorhinostomy (DCR), the method including:

inserting a nasal guide component of a dacryocystorhinostomy (DCR) guide into a nasal cavity of a patient's body, wherein the nasal guide component, including a distal guide tip thereof, is shaped so as to define a nasal guidewire-accepting channel;

forming a bypass between a lacrimal sac and the nasal cavity; and thereafter, placing a guidewire such that the guidewire passes through a lacrimal passageway, the bypass, and at least a portion of the nasal guidewire-accepting channel, the lacrimal passageway including punctum, a lacrimal canal, and a common canaliculus.

For some applications, placing the guidewire includes placing the guidewire such that the guidewire passes through the lacrimal passageway, the bypass, the entire nasal guidewire-accepting channel, and out of a proximal end of the nasal guidewire-accepting channel.

For some applications, placing the guidewire such that the guidewire passes through the lacrimal passageway includes: advancing a lacrimal guidewire shaft through a guide channel of a lacrimal guide component of the DCR guide, the lacrimal passageway, and the bypass, until a distal tip of the lacrimal guidewire shaft is in contact with the distal guide tip of the nasal guide component, wherein the DCR guide constrains the distal guide tip of the nasal guide component to fall in a path of advancement of the distal tip; and advancing the guidewire through a lacrimal guidewire-accepting channel of the lacrimal guidewire shaft while (a) the lacrimal guidewire shaft is disposed passing through the lacrimal passageway and the bypass, and (b) the distal tip of the lacrimal guidewire shaft is in contact with the distal guide tip of the nasal guide component. For some applications, a distal opening of the nasal guidewire-accepting channel faces at least partially in a lateral direction that faces toward the lacrimal guide component. For some applications, inserting the nasal guide component and the lacrimal guide component includes using DCR guide to set a desired angle between respective central longitudinal axes of the nasal guide component and the lacrimal guidewire shaft. For some applications, setting the desired angle includes using an arcuate portion of the DCR guide that allows relative movement between the nasal guide component and the lacrimal guide component to set the desired angle.

For some applications, placing the guidewire includes placing the guidewire such that a first end of the guidewire extends out of the patient's body through the lacrimal punctum and a second end of the guidewire, opposite the first end, extends out of the patient's body through the nasal cavity.

For some applications, the method further includes, after placing the guidewire: removing the lacrimal guidewire shaft from the patient's body; advancing a dilator along and over the guidewire and through the lacrimal passageway and into the bypass; and dilating the bypass using the dilator. For some applications, the dilator includes an inflatable element, and dilating the bypass includes inflating the inflatable element in the bypass. For some applications, the method further includes, after dilating the bypass: advancing a tubular support element along and over the guidewire and through the lacrimal passageway and into the bypass; and removing the guidewire from the patient's body while leaving the tubular support element in place in the bypass.

There is still further provided, in accordance with an application of the present invention, apparatus for performing dacryocystorhinostomy (DCR), the apparatus including a dacryocystorhinostomy (DCR) tool, which includes:

a perforating shaft having a distal perforating tip configured to form a bypass between a lacrimal sac and a nasal cavity through a lateral side of the lacrimal sac, a lacrimal bone, and nasal mucosa; and a DCR guide, which includes:
a nasal guide component, which is configured to be inserted into the nasal cavity and has a distal guide tip; and
a lacrimal guide component, which is shaped so as to define a guide channel that is configured to orient the DCR guide with respect to the distal perforating tip of the perforating shaft during advancing of the distal perforating tip through a lacrimal passageway and into the lacrimal sac, until contact of the distal perforating tip with the distal guide tip of the nasal guide component blocks further advancing of the distal perforating tip, the lacrimal passageway including a lacrimal punctum, a lacrimal canal, and a common canaliculus, wherein the DCR guide is configured to constrain the distal guide tip of the nasal guide component to fall in a path of advancement of the distal perforating tip.

For some applications, the DCR guide is configured to set a desired angle between respective central longitudinal axes of the nasal guide component and the perforating shaft.

For some applications, the DCR guide is shaped so as to define an arcuate portion that is configured to allow relative movement between the nasal guide component and the lacrimal guide component to set the desired angle.

For some applications, the distal perforating tip is shaped as a drill bit.

For some applications, the distal perforating tip is shaped as a punch.

For some applications, the nasal guide component, including the distal guide tip, is shaped so as to define a nasal guidewire-accepting channel.

For some applications, a distal opening of the nasal guidewire-accepting channel faces at least partially in a lateral direction that faces toward the lacrimal guide component.

For some applications:

the nasal guide component includes (a) an outer guide element that is shaped so as to define a nasal-shaft-accepting channel therethrough, and (b) a nasal shaft that is slidable through the nasal-shaft-accepting channel, and the nasal shaft is shaped so as to define the distal guide tip and the nasal guidewire-accepting channel, and when the outer guide element and the nasal shaft are coupled together, a distal opening of the nasal guidewire-accepting channel is constrained by the outer guide element and the nasal shaft to face at least partially in a lateral direction that faces toward the lacrimal guide component.

For some applications, the nasal guide component includes a locking mechanism, which is configured to lock the nasal shaft rotationally with respect to the nasal-shaft-accepting channel, thereby maintaining the distal opening of the nasal guidewire-accepting channel facing at least partially in the lateral direction.

For some applications, the perforating shaft, including the distal perforating tip, is shaped so as to define a lacrimal guidewire-accepting channel.

For some applications:

the DCR tool further includes a lacrimal guidewire shaft having a distal tip, and the lacrimal guidewire shaft, including the distal tip thereof, is shaped so as to define a lacrimal guidewire-accepting channel, the guide channel of the lacrimal guide component is configured to orient the DCR guide with respect to the distal tip of the lacrimal guidewire shaft during advancing of the distal tip through the guide channel and the lacrimal passageway and into the lacrimal sac, and the DCR guide is configured to constrain the distal guide tip of the nasal guide component to fall in a path of advancement of the distal tip of the lacrimal guidewire shaft.

For some applications, the DCR tool further includes a dilator, which is configured to be advanced through the lacrimal passageway and into the bypass, and to dilate the bypass.

For some applications, the dilator includes an inflatable element, which is configured to dilate the bypass by being inflated in the bypass.

For some applications, the apparatus further includes a tubular support element, which is configured to be advanced through the lacrimal passageway and into the bypass, and to maintain patency of the bypass.

For any of the applications described hereinabove, the nasal guide component may include (a) an outer guide element that is shaped so as to define a nasal-shaft-accepting channel therethrough, and (b) a nasal shaft that is slidable through the nasal-shaft-accepting channel, and the nasal shaft may be shaped so as to define the distal guide tip.

There is additionally provided, in accordance with an application of the present invention, apparatus for performing dacryocystorhinostomy (DCR), the apparatus for use with a guidewire and including a dacryocystorhinostomy (DCR) tool, which includes:

a lacrimal guidewire shaft, which is configured to be inserted into a lacrimal passageway and has a distal tip, wherein the lacrimal guidewire shaft, including the distal tip, is shaped so as to define a lacrimal guidewire-accepting channel, and wherein the lacrimal passageway includes a lacrimal punctum, a lacrimal canal, and a common canaliculus; and a DCR guide, which includes:

a nasal guide component, which is configured to be inserted into the nasal cavity and has a distal guide tip, wherein the nasal guide component, including the distal guide tip, is shaped so as to define a nasal guidewire-accepting channel; and a lacrimal guide component, which is shaped so as to define a guide channel that is configured to orient the DCR guide with respect to the distal tip of the lacrimal guidewire shaft during advancing of the distal tip through the lacrimal passageway and into a lacrimal sac, until contact of the distal tip of the lacrimal guidewire shaft with the distal guide tip of the nasal guide component blocks further advancing of the distal tip of the lacrimal guidewire shaft, wherein the DCR guide is configured to constrain the distal guide tip of the nasal guide component to fall in a path of advancement of the distal tip of the lacrimal guidewire shaft.

For some applications, the DCR guide is configured to set a desired angle between respective central longitudinal axes of the nasal guide component and the lacrimal guidewire shaft.

For some applications, the DCR guide is shaped so as to define an arcuate portion that is configured to allow relative movement between the nasal guide component and the lacrimal guide component to set the desired angle.

For some applications, a distal opening of the nasal guidewire-accepting channel faces at least partially in a lateral direction that faces toward the lacrimal guide component.

For some applications:

the nasal guide component includes (a) an outer guide element that is shaped so as to define a nasal-shaft-accepting channel therethrough, and (b) a nasal shaft that is slidable through the nasal-shaft-accepting channel, and the nasal shaft is shaped so as to define the distal guide tip and the nasal guidewire-accepting channel, and when the outer guide element and the nasal shaft are coupled together, a distal opening of the nasal guidewire-accepting channel is constrained by the outer guide element and the nasal shaft to faces at least partially in a lateral direction that faces toward the lacrimal guide component.

For some applications, the nasal guide component includes a locking mechanism, which is configured to lock the nasal shaft rotationally with respect to the nasal-shaft-accepting channel, thereby maintaining the distal opening of the nasal guidewire-accepting channel facing at least partially in the lateral direction.

The present invention will be more fully understood from the following detailed description of embodiments thereof, taken together with the drawings, in which:

DETAILED DESCRIPTION OF APPLICATIONS

Figure 1:
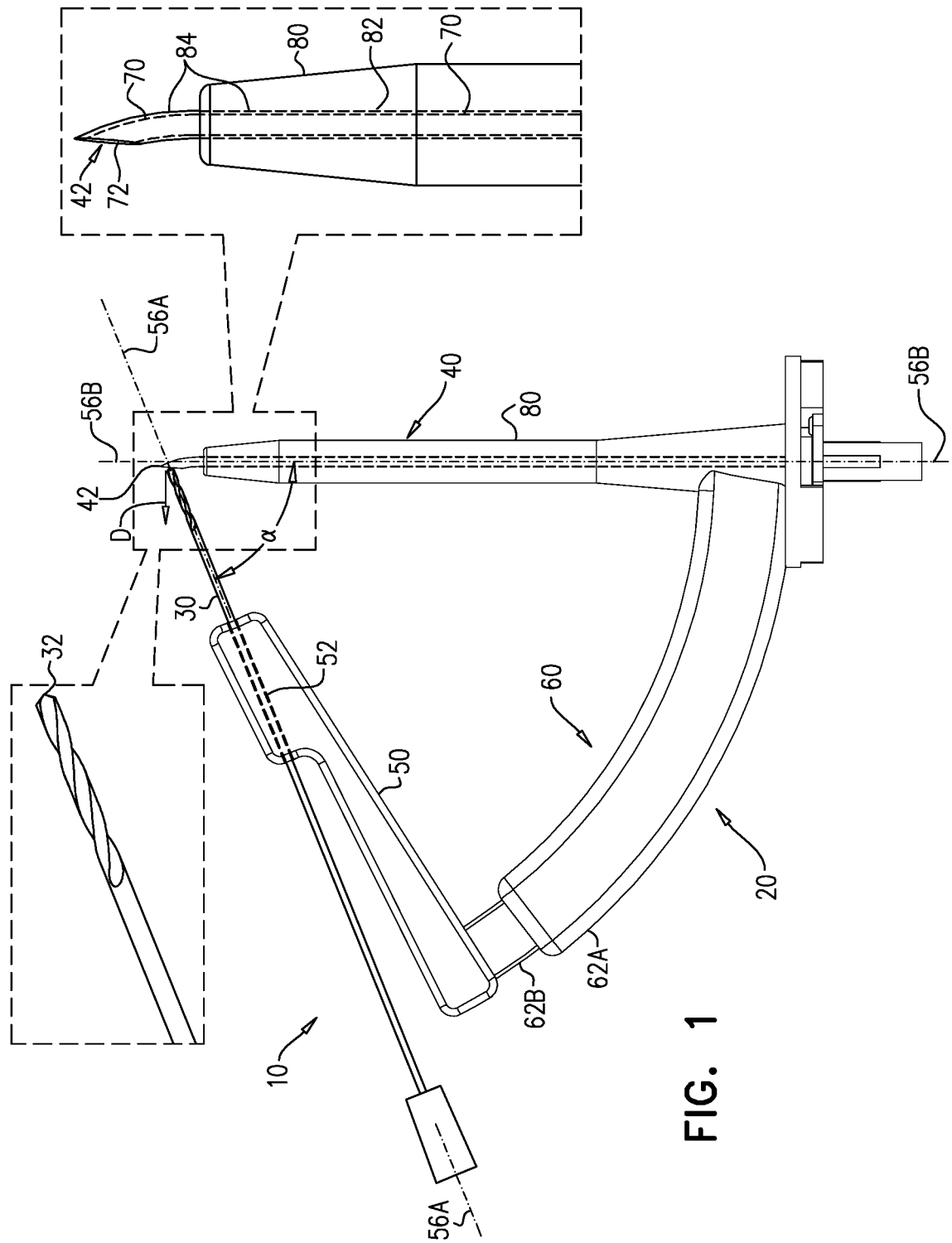
FIG. 1 is a schematic illustration of a dacryocystorhinostomy (DCR) tool, in accordance with an application of the present invention.

FIG. 1 is a schematic illustration of a dacryocystorhinostomy (DCR) tool 10, in accordance with an application of the present invention. the DCR tool is used to perform dacryocystorhinostomy (DCR), i.e., the formation of a bypass between the lacrimal system and the nasal cavity. DCR tool 10 comprises a dacryocystorhinostomy (DCR) guide 20 and, for some applications, a perforating shaft 30 having a distal perforating tip 32 configured to form a bypass between a lacrimal sac and a nasal cavity through a lateral side of the lacrimal sac, a lacrimal bone, and nasal mucosa, such as described hereinbelow with reference to FIGS. 4A-B.

Figure 4A:
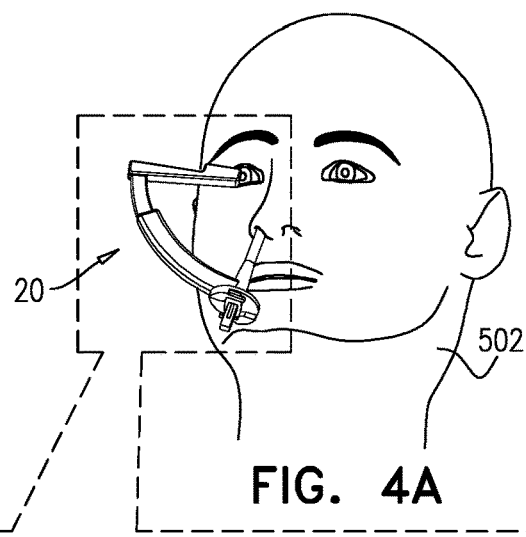
FIGS. 4A-I are schematic illustrations of the performance of the method of FIG. 3, in accordance with an application of the present invention.
Figure 4A:
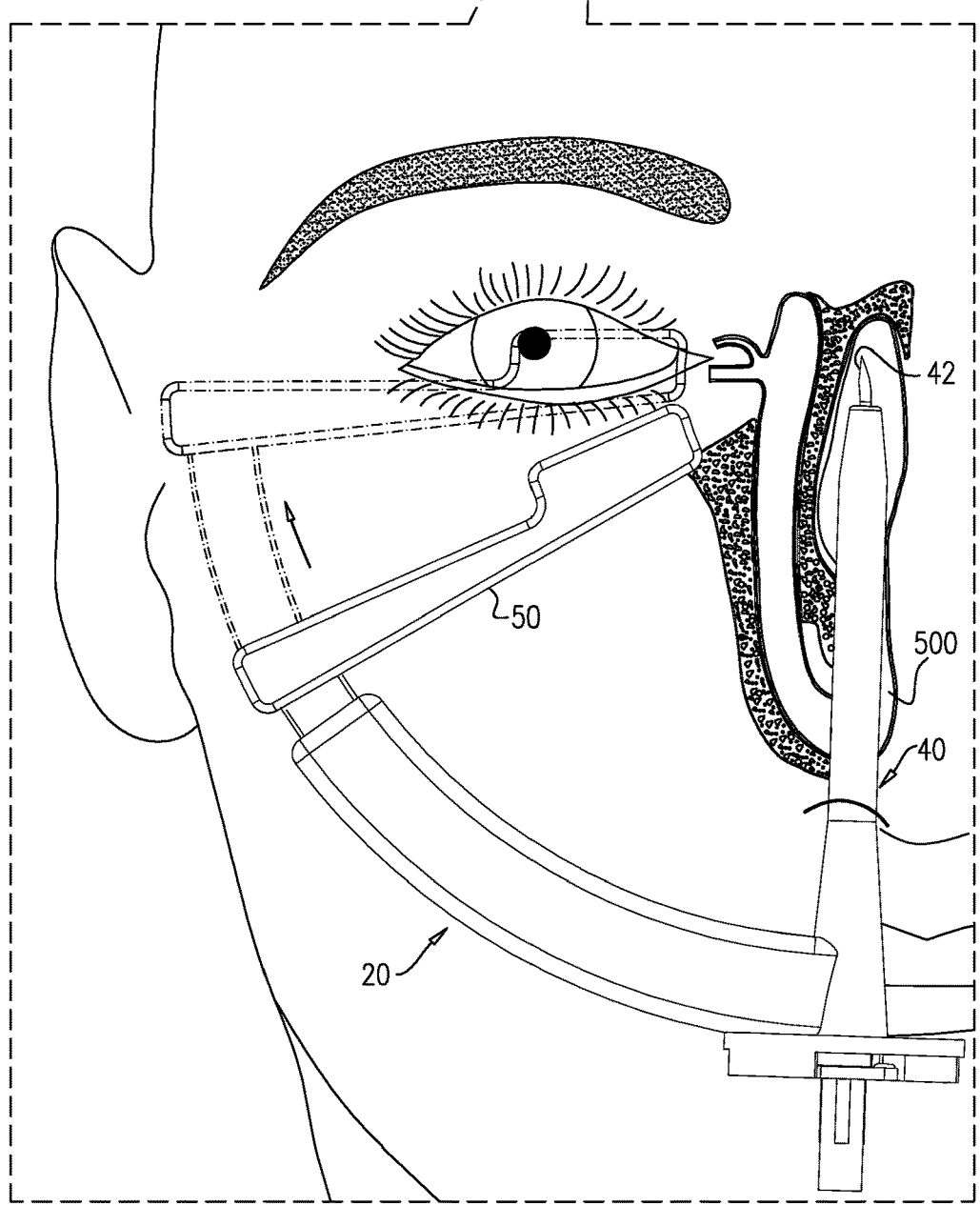
Figure 4B:
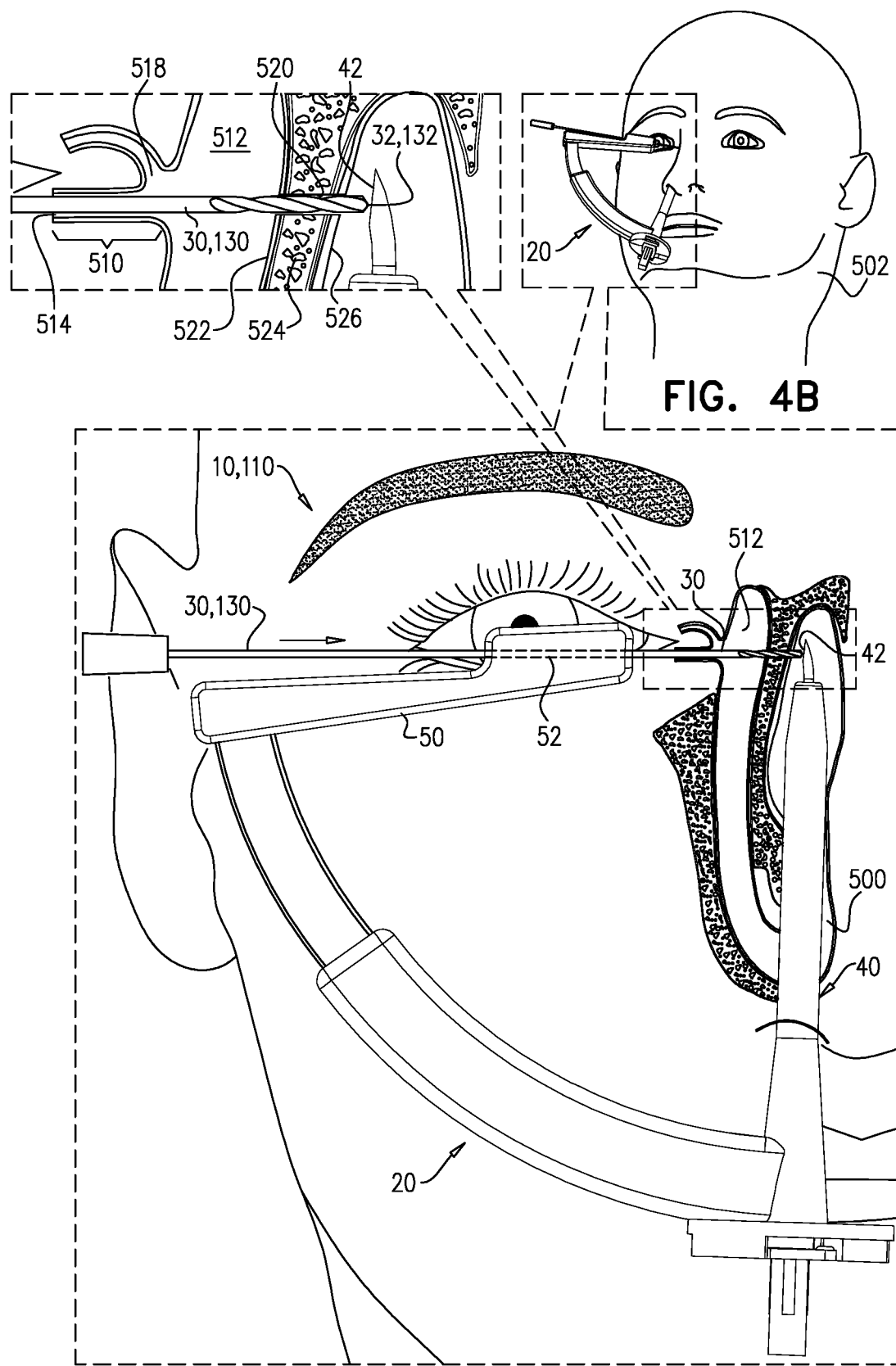

DCR guide 20 comprises:
- a nasal guide component 40, which is configured to be inserted into the nasal cavity and has a distal guide tip 42; and
- a lacrimal guide component 50, which is shaped so as to define a guide channel 52, which is configured to orient DCR guide 20 (via lacrimal guide component 50) with respect to guide distal perforating tip 32 of perforating shaft 30 during advancing of distal perforating tip 32 through a lacrimal passageway and into a lacrimal sac, such as described hereinbelow with reference to FIG. 4A-B, until contact of distal perforating tip 32 with distal guide tip 42 of nasal guide component 40 blocks further advancing of distal perforating tip 32, such as described hereinbelow with reference to FIG. 4B.

DCR guide 20 is configured to constrain distal guide tip 42 of nasal guide component 40 to fall in a path of advancement of distal perforating tip 32. The lacrimal passageway to a large extent sets the path of advancement of distal perforating tip 32, which in turn sets an orientation and location of perforating shaft 30. Perforating shaft 30 in turn sets an orientation and location of lacrimal guide component 50, which sets an orientation and location of nasal guide component 40, including distal guide tip 42, in the nasal cavity (as described in more detail hereinbelow with reference to FIG. 4B). As a result, distal guide tip 42 is automatically and non-electrically positioned in the path of advancement of distal perforating tip 32, and thus comes in contact with distal perforating tip 32 and blocks its advancement. Typically, DCR guide 20 does not comprise any circuitry or other electrical or electronic elements.

Reference is still made to FIG. 1. For some applications, DCR guide 20 (e.g., a support structure thereof) is configured to set a desired angle α (alpha) between respective central longitudinal axes 56A and 56B of nasal guide component 40 and perforating shaft 30. For some of these applications, DCR guide 20 (e.g., a support structure thereof) is shaped so as to define an arcuate portion 60 that is configured to allow relative movement between nasal guide component 40 and lacrimal guide component 50 to set the desired angle α (alpha). For some applications, DCR guide 20 comprises first and second arcuate support members 62A and 62B, which are coupled in fixed orientation to nasal guide component 40 and lacrimal guide component 50, respectively, and together define arcuate portion 60. First and second arcuate support members 62A and 62B are arranged in slidable attachment with respect to one other so as to set a total aggregate length of an arc defined by the support members and thus angle α (alpha). For example, one of first and second arcuate support members 62A and 62B may be partially disposed within the other of first and second arcuate support members 62A and 62B, as shown, or first and second arcuate support members 62A and 62B be disposed alongside one another in slidable attachment.

Reference is still made to FIG. 1. For some applications, nasal guide component 40, including distal guide tip 42, is shaped so as to define a nasal guidewire-accepting channel 70. Typically, a distal opening 72 of nasal guidewire-accepting channel 70 faces at least partially in a lateral direction D that faces toward lacrimal guide component 50 (typically, this orientation is set (i.e., constrained) by DCR guide 20, such as described hereinbelow with reference to FIGS. 5A-D). (As used in the present application, including in the claims, the phrase "faces toward" does not require the lateral direction D to be directed entirely toward lacrimal guide component 50.)

Reference is still made to FIG. 1. For some applications, nasal guide component 40 comprises (a) an outer guide element 80 that is shaped so as to define a nasal-shaft-accepting channel 82 therethrough, and (b) a nasal shaft 84 that is slidable through nasal-shaft-accepting channel 82, typically before nasal guide component 40 is inserted into the nasal cavity. Nasal shaft 84 is shaped so as to define distal guide tip 42 and nasal guidewire-accepting channel 70, if provided. For some applications, as shown, nasal shaft 84 comprises a needle, which, for example, may be a Tuohy needle, as is known in the epidural art. As mentioned above, distal opening 72 of nasal guidewire-accepting channel 70 typically faces at least partially in lateral direction D. For some applications, DCR guide 20 is configured to rotationally orient distal guide tip 42 such that lateral direction D faces toward lacrimal guide component 50. For some applications, nasal guide component 40 further comprises a locking mechanism 600, such as described hereinbelow with reference to FIGS. 5A-D.

Figure 2A:
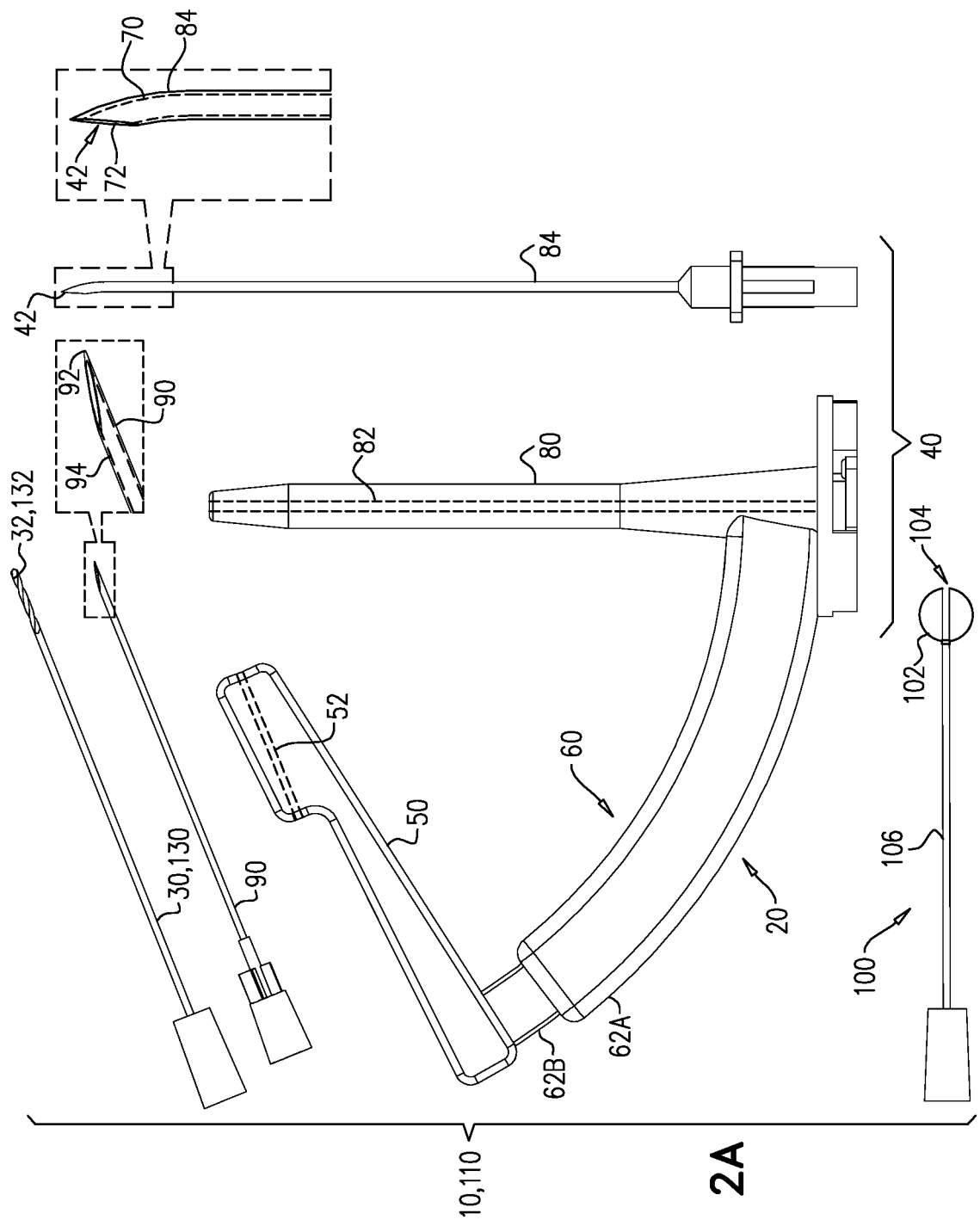
FIGS. 2A-C are schematic illustrations of components of respective DCR tools, in accordance with respective applications of the present invention.
Figure 2B:
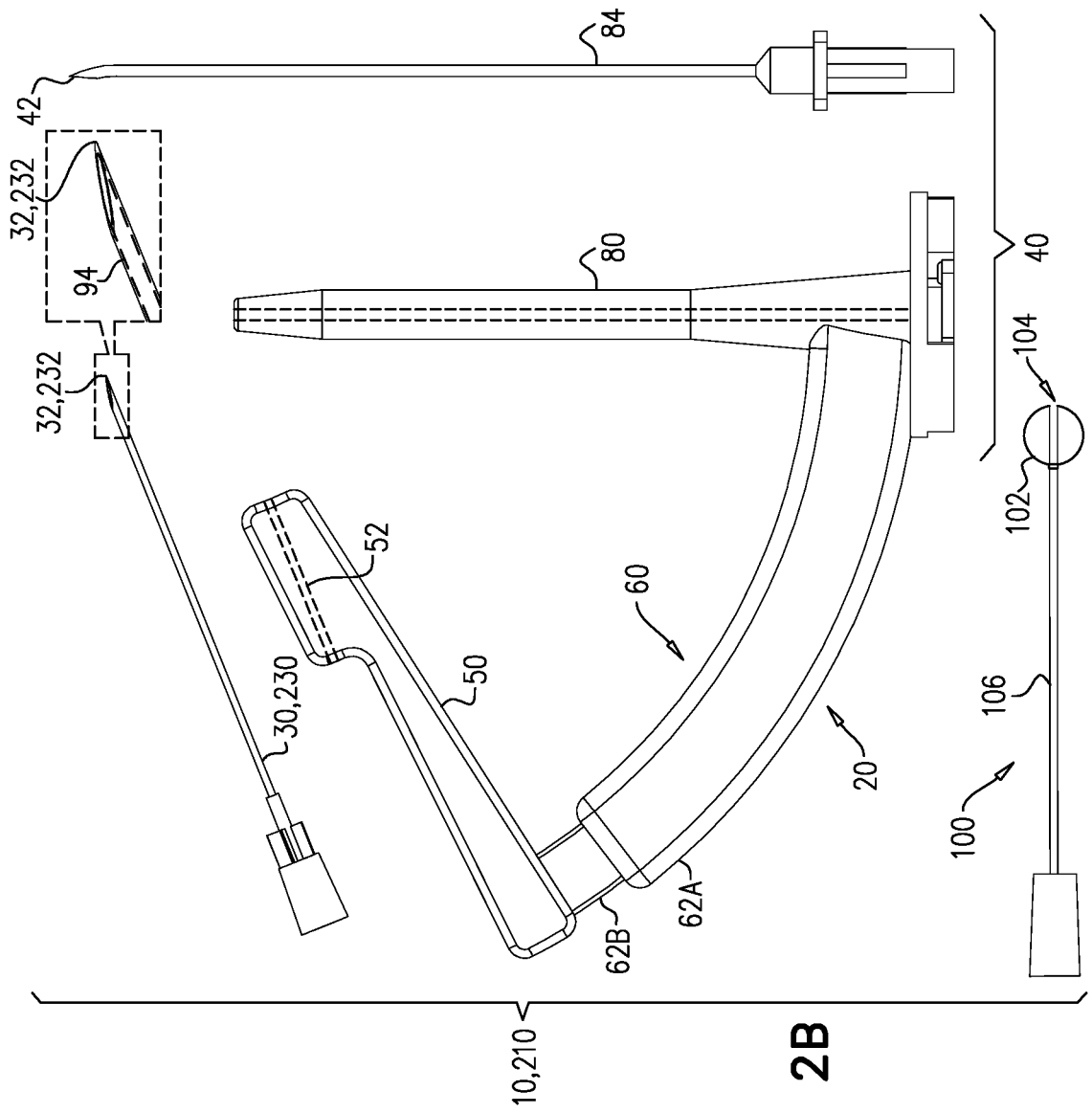
Figure 2C:
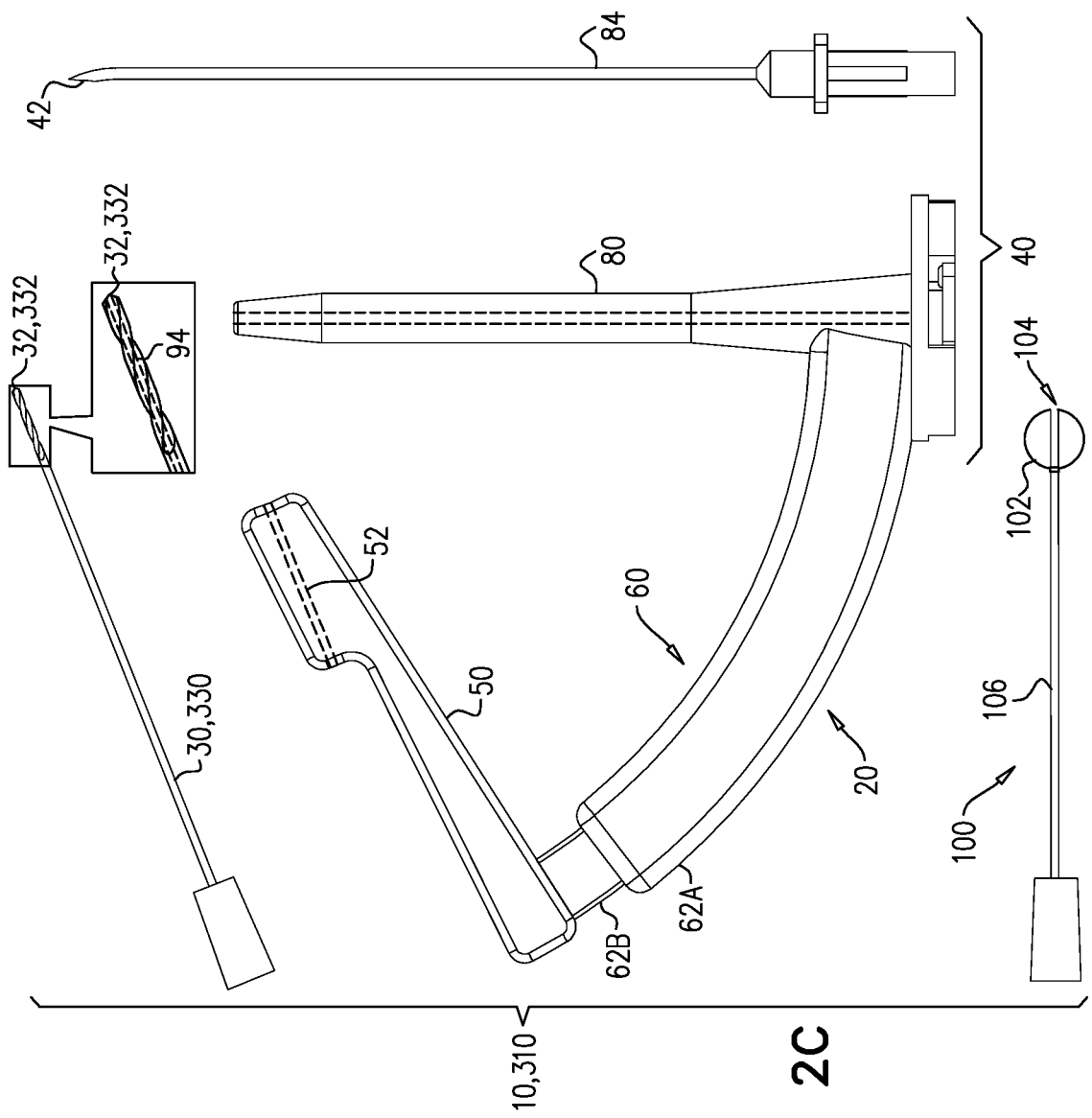

Reference is now made to FIGS. 2A-C, which are schematic illustrations of components of DCR tools 110, 210, and 310, respectively, in accordance with respective applications of the present invention. DCR tools 110, 210, and 310 are implementations of DCR tool 10, described hereinabove with reference to FIG. 1 and may implement any of the features thereof.

For some applications, DCR tool 10 further comprises a dilator 100, which is configured to be advanced through the lacrimal passageway and into the bypass, and to dilate the bypass. For some of these applications, dilator 100 comprises an inflatable element 102, such as a balloon, which is configured to dilate the bypass by being inflated in the bypass. Typically, inflatable element 102 is disposed at or near a distal end 104 of a shaft 106 of dilator 100. Dilator 100 is typically inflated about 12 mm medially from a lacrimal punctum 514, and typically has a length of 10-15 mm. For other applications, DCR tool 10 does not comprise dilator 100.

Reference is made to FIG. 2A. In this configuration, DCR tool 110 further comprises, in addition to perforating shaft 30, a lacrimal guidewire shaft 90 having a distal tip 92 (which is either sharp, as shown, or blunt). In this configuration, perforating shaft 30 is typically solid, i.e., does not define a channel therethrough. For some applications, perforating shaft 30 comprises a drilling perforating shaft 130, and distal perforating tip 32 of perforating shaft 30 is shaped as a drill bit 132. For other applications, perforating shaft 30 comprises a punching perforating shaft, and distal perforating tip 32 is shaped as a punch (configuration not shown, but similar to punching perforating shaft 230 described hereinbelow with reference to FIG. 2B, except that in the present configuration the punching perforating shaft does not necessarily define a channel therethrough). Further alternatively, perforating shaft 30 comprises an energy-application perforating shaft, which uses energy (e.g., RF, electrical, or laser) to form the bypass.

Reference is still made to FIG. 2A. Lacrimal guidewire shaft 90, including distal tip 92 thereof, is shaped so as to define a lacrimal guidewire-accepting channel 94. Guide channel 52 of lacrimal guide component 50 is configured to orient DCR guide 20 (via lacrimal guide component 50) with respect to distal tip 92 of lacrimal guidewire shaft 90 during advancing of distal tip 92 through guide channel 52 and the lacrimal passageway and into the lacrimal sac. DCR guide 20 is configured to constrain distal guide tip 42 of nasal guide component 40 to fall in a path of advancement of distal tip 92 of lacrimal guidewire shaft 90.

Reference is still made to FIG. 2A. For some applications, DCR tool 110 does not comprise perforating shaft 30. For these applications, the surgeon forms bypass using a perforating tool that is not a component of DCR tool 110, either using or not using DCR tool 110.

Reference is made to FIGS. 2B and 2C. In these configurations, perforating shaft 30, including distal perforating tip 32, is shaped so as to define lacrimal guidewire-accepting channel 94. In the configuration shown in FIG. 2B, perforating shaft 30 of DCR tool 220 comprises a punching perforating shaft 230, and distal perforating tip 32 is shaped as a punch 232. In the configuration shown in FIG. 2C, perforating shaft 30 of DCR tool 320 comprises a drilling perforating shaft 330, and distal perforating tip 32 is shaped as a drill bit 332.

For some applications, a tubular support element 96 is provided, which is configured to be advanced through the lacrimal passageway and into the bypass, and to maintain patency of the bypass, such as described hereinbelow with reference to FIG. 4H.

Figure 3:
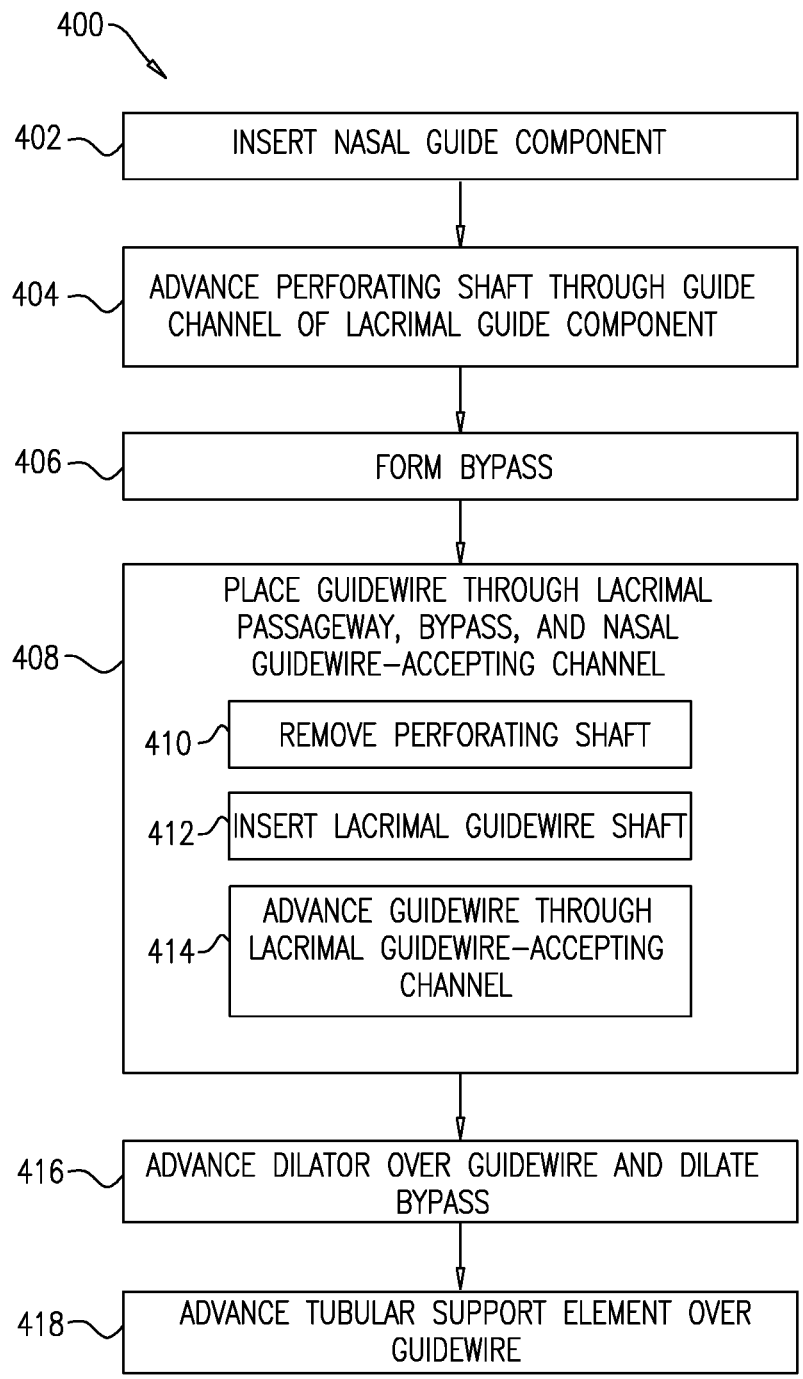
FIG. 3 is a flowchart illustrating a method of performing dacryocystorhinostomy (DCR), in accordance with an application of the present invention.

Reference is now made to FIG. 3, which is a flowchart illustrating a method 400 of performing dacryocystorhinostomy (DCR), in accordance with an application of the present invention. Reference is also made to FIGS. 4A-I, which are schematic illustrations of the performance of method 400, in accordance with an application of the present invention. Method 400 is illustrated using DCR tool 110, described hereinabove with reference to FIG. 2A. DCR tool 210 or DCR tool 310, described hereinabove with reference to FIGS. 2B and 2C, respectively, may alternatively be used, mutatis mutandis, such as described hereinbelow.

As shown in FIG. 4A, at a nasal guide insertion step 402, nasal guide component 40 of DCR guide 20 is inserted into a nasal cavity 500 of a patient's body 502. Nasal guide component 40 need not be inserted precisely by the surgeon, so long as it is inserted into the correct nostril, because it will be precisely oriented and positioned by DCR guide 20 at lacrimal advancement step 404, described hereinbelow with reference to FIG. 4B.

As shown in FIG. 4B, at a lacrimal advancement step 404, perforating shaft 30 is advanced through guide channel 52 of lacrimal guide component 50 of DCR guide 20 and a lacrimal passageway 510 and into a lacrimal sac 512. Lacrimal passageway 510 includes lacrimal punctum 514 (either inferior, as shown, or superior, not shown), a lacrimal canal 516 (either inferior, as shown, or superior, not shown), and a common canaliculus 518. Surgeons skilled in the DCR art generally are able to advance perforating shaft 30 through lacrimal passageway 510 without difficulty.

DCR guide 20 constrains distal guide tip 42 of nasal guide component 40 to fall in a path of advancement of distal perforating tip 32. As a result of this constraint, DCR guide 20 typically positions distal guide tip 42 of nasal guide component 40 at an axilla of a middle turbinate of nasal cavity 500. Optionally, the surgeon may visually confirm the proper positioning of distal guide tip 42, such as using a nasal endoscope.

For some applications, such as shown in the transition between FIG. 4A and FIG. 4B, for performing nasal guide insertion step 402 and lacrimal advancement step 404, DCR guide 20 is used to set a desired angle α (alpha) between respective central longitudinal axes 56A and 56B of nasal guide component 40 and perforating shaft 30, such as described hereinabove with reference to FIG. 1, based on the particular anatomy of the patient (e.g., the shape and size of the relevant parts of the anatomy). For some applications, the desired angle α (alpha) is set using arcuate portion 60 of DCR guide 20 that allows relative movement between nasal guide component 40 and lacrimal guide component 50 to set the desired angle, such as described hereinabove with reference to FIG. 1.

Also as shown in FIG. 4B, at a perforation step 406, a bypass 520 is formed between lacrimal sac 512 and nasal cavity 500 by advancing distal perforating tip 32 of perforating shaft 30 through a lateral side 522 of lacrimal sac 512, a lacrimal bone 524, and nasal mucosa 526, until contact of distal perforating tip 32 with distal guide tip 42 of nasal guide component 40 blocks further advancing of distal perforating tip 32. This contact prevents over-advancement distal perforating tip 32, which might otherwise perforate tissue across nasal cavity 500, which is generally no more than several millimeters beyond bypass 520. For some applications, such as shown in FIG. 4B, distal perforating tip 32 is drilled through the lateral side of lacrimal sac 512, lacrimal bone 524, and nasal mucosa 526. Alternatively, distal perforating tip 32 is punched through the lateral side of lacrimal sac 512, lacrimal bone 524, and nasal mucosa 526 (technique not shown in FIG. 4B).

Lacrimal advancement step 404 and perforation step 406 are optional; the surgeon may instead form bypass 520 using a perforating tool that is not a component of DCR tool 110 (e.g., either mechanically or using energy, e.g., laser energy), either using or not using DCR tool 110.

Figure 4C:
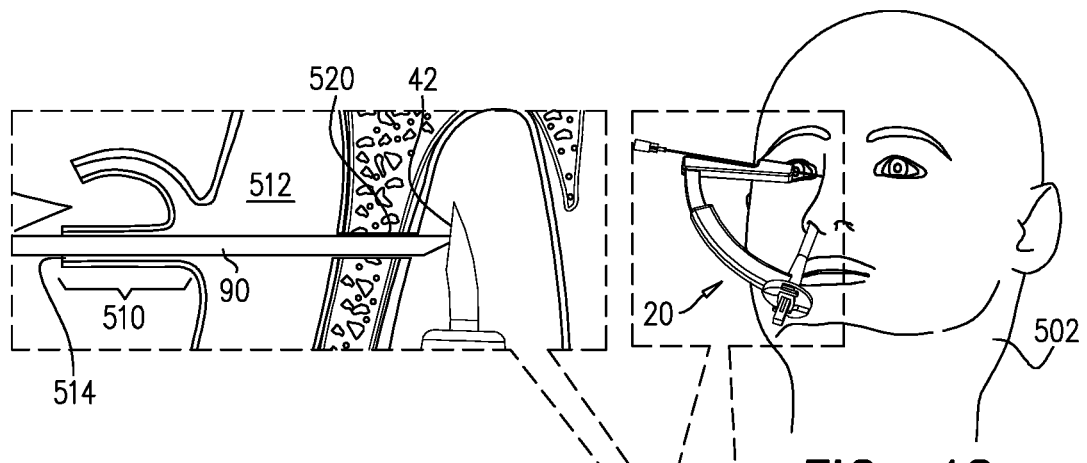
Figure 4C:
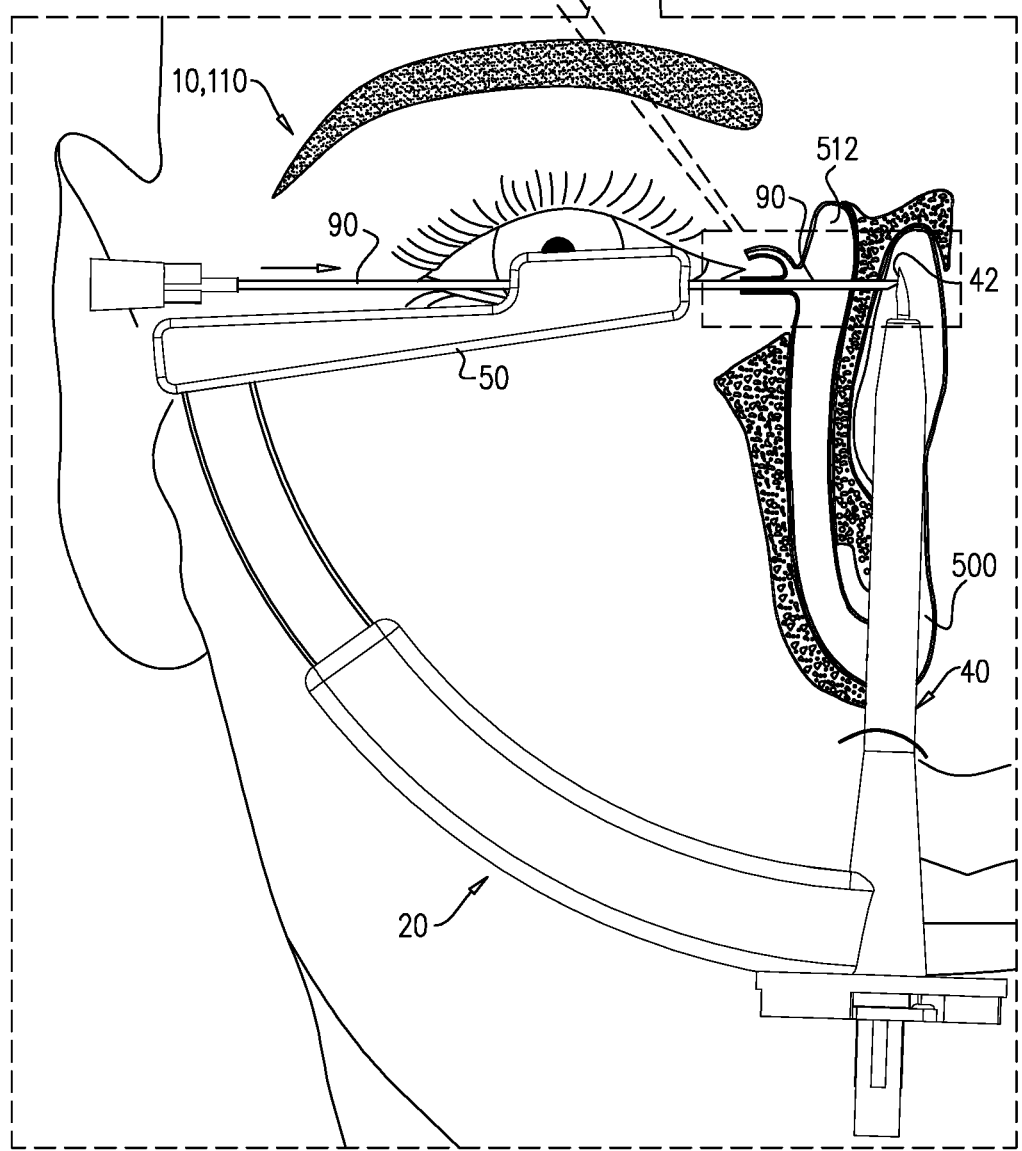
Figure 4D:
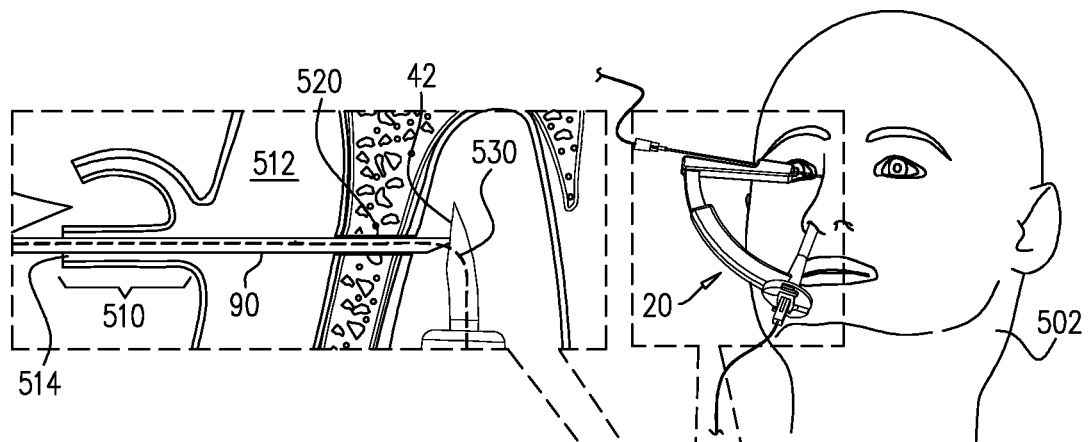
Figure 4D:
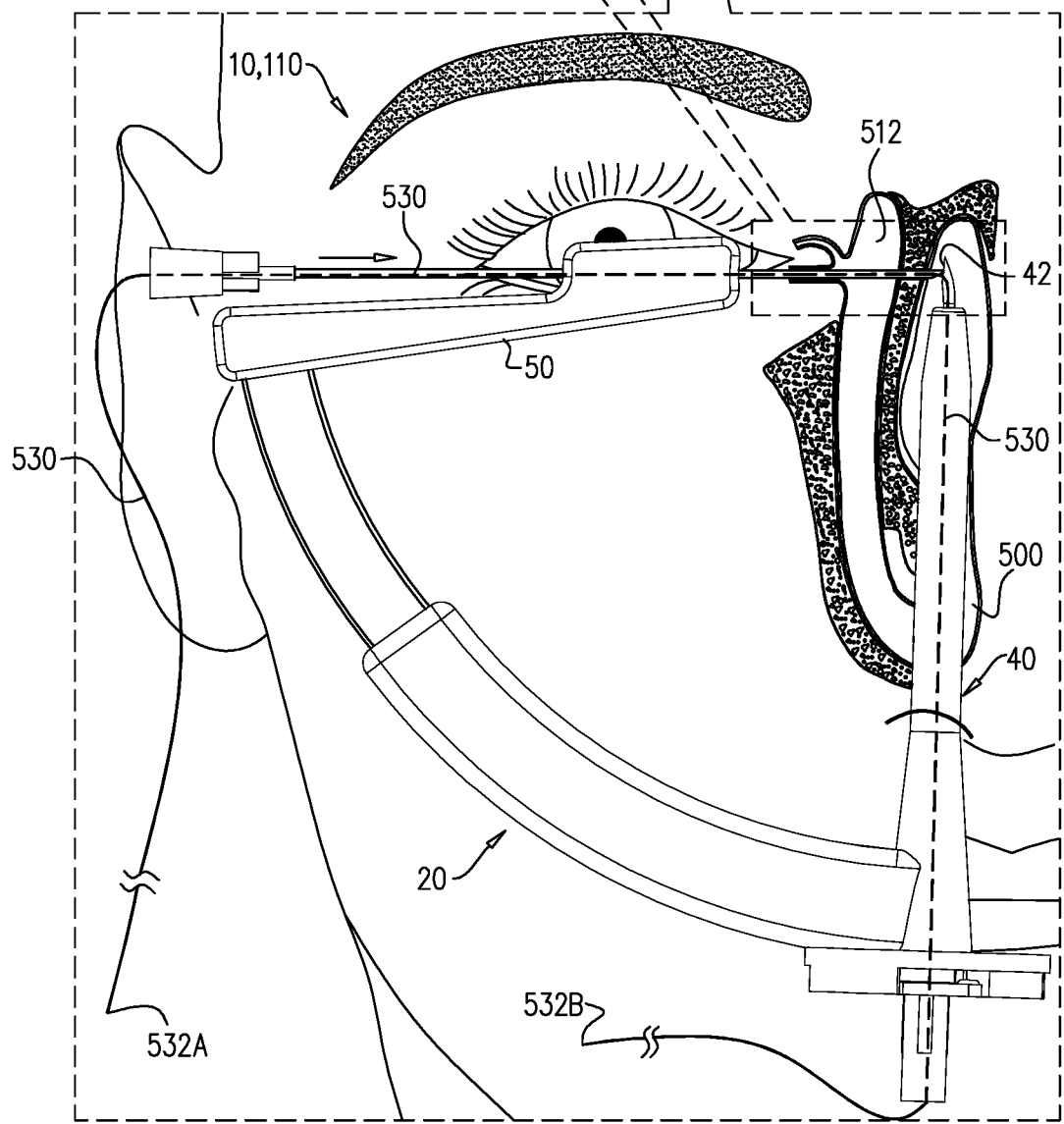
Figure 4E:
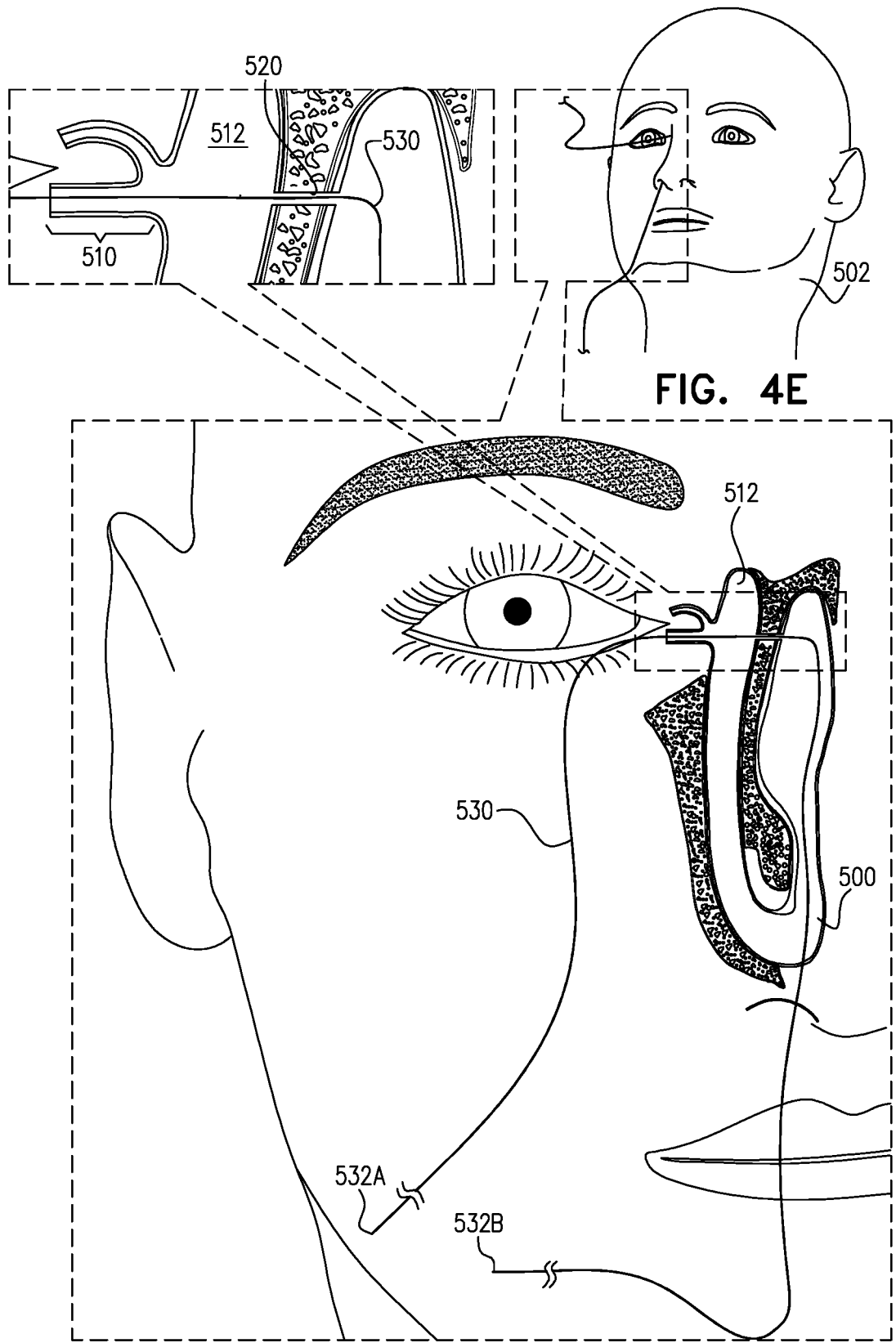

For some applications, as shown in FIGS. 4C-E, at a guidewire placement step 408, a guidewire 530 is placed such that guidewire 530 passes through lacrimal passageway 510, bypass 520, and at least a portion of nasal guidewire-accepting channel 70 (labeled in FIGS. 1 and 2A). (In these applications, nasal guide component 40, including distal guide tip 42, is shaped so as to define nasal guidewire-accepting channel 70.) Typically, guidewire 530 is advanced in a direction from lacrimal punctum 514 toward nasal cavity 500. Typically, guidewire 530 is placed such that guidewire 530 passes through lacrimal passageway 510, bypass 520, the entire nasal guidewire-accepting channel 70, and out of a proximal end of nasal guidewire-accepting channel 70. Typically, distal opening 72 of nasal guidewire-accepting channel 70 faces at least partially in lateral direction D that faces toward lacrimal guide component 50, such as described hereinabove with reference to FIG. 1.

For some applications, guidewire placement step 408 comprises:
  at a perforating shaft removal step 410, removing perforating shaft 30 from the patient's body (after forming bypass 520, as shown in FIG. 4B);

as shown in FIG. 4C, at a lacrimal guidewire insertion step 412, inserting lacrimal guidewire shaft 90 through guide channel 52 of lacrimal guide component 50 and lacrimal passageway 510 and into lacrimal sac 512; DCR guide 20 constrains distal guide tip 42 of nasal guide component 40 to fall in a path of advancement of distal tip 92 of lacrimal guidewire shaft 90 (as describe hereinabove with reference to FIG. 2A, lacrimal guidewire shaft 90, including distal tip 92 thereof, is shaped so as to define lacrimal guidewire-accepting channel 94);

as shown in FIG. 4D, at a guidewire advancement step 414, advancing guidewire 530 through lacrimal guidewire-accepting channel 94 while lacrimal guidewire shaft 90 is disposed passing through lacrimal passageway 510; and withdrawing lacrimal guide component 50, lacrimal guidewire shaft 90, and nasal guide component 40 from guidewire 530 and out of the patient's body, leaving guidewire 530 in place, as shown in FIG. 4E, typically such that a first end 532A of guidewire 530 extends out of the patient's body through lacrimal punctum 514 and a second end 532B of guidewire 530, opposite first end 532A, extends out of the patient's body through nasal cavity 500.

Typically, as shown in FIG. 4D, at guidewire advancement step 414, guidewire 530 is advanced through lacrimal guidewire-accepting channel 94 while (a) lacrimal guidewire shaft 90 is disposed passing through lacrimal passageway 510 and bypass 520, and (b) distal tip 92 of lacrimal guidewire shaft 90 is in contact with distal guide tip 42 of nasal guide component 40.

Figure 4F:
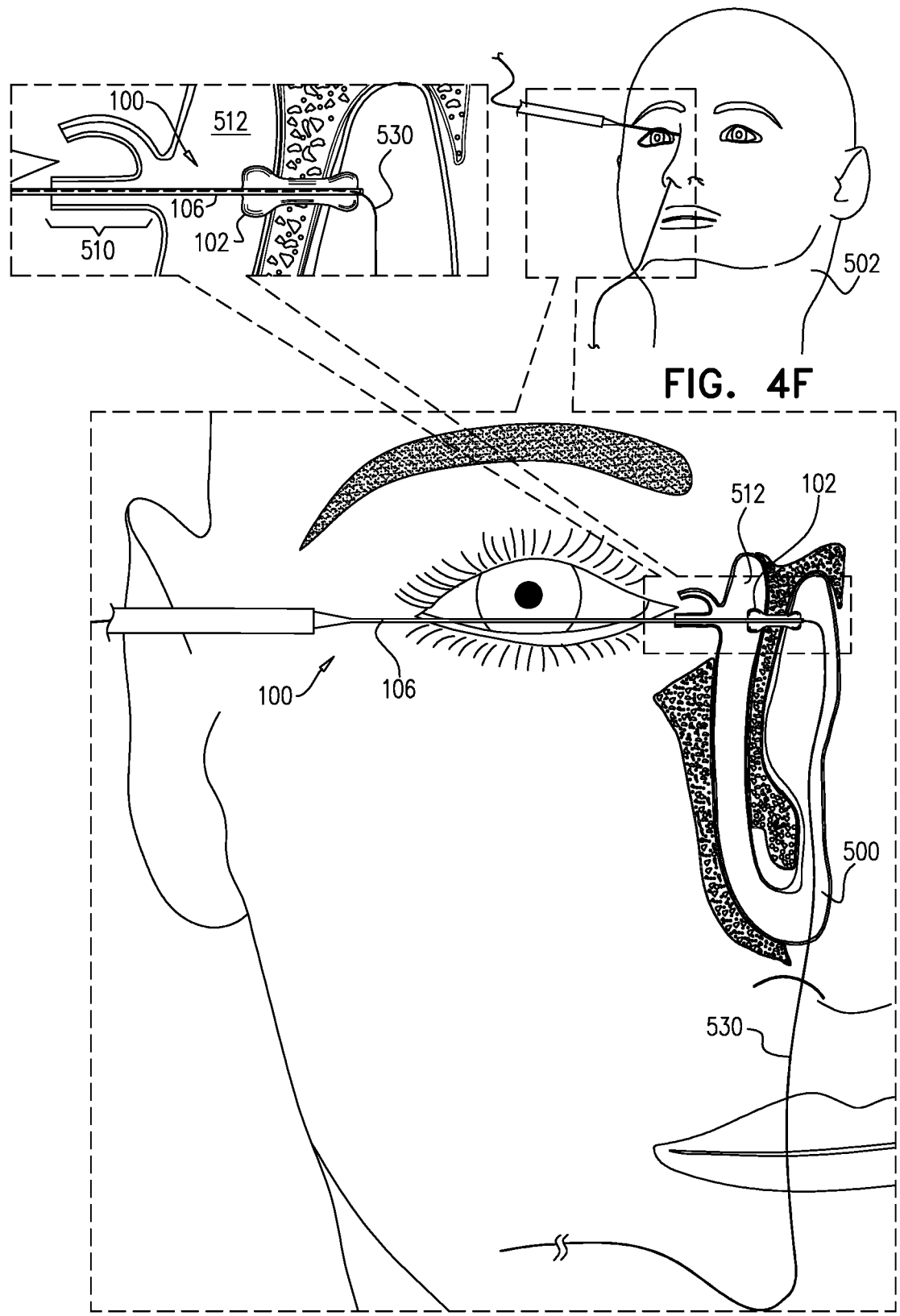
Figure 4G:
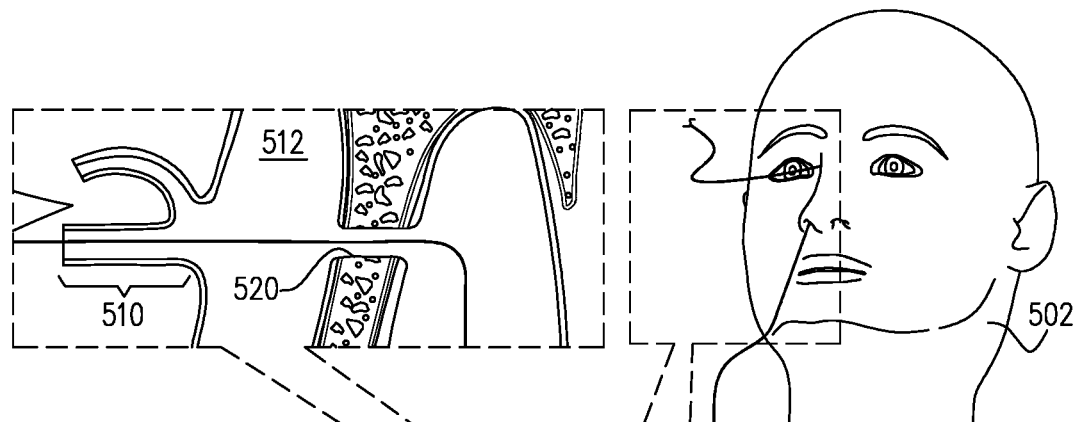
Figure 4G:
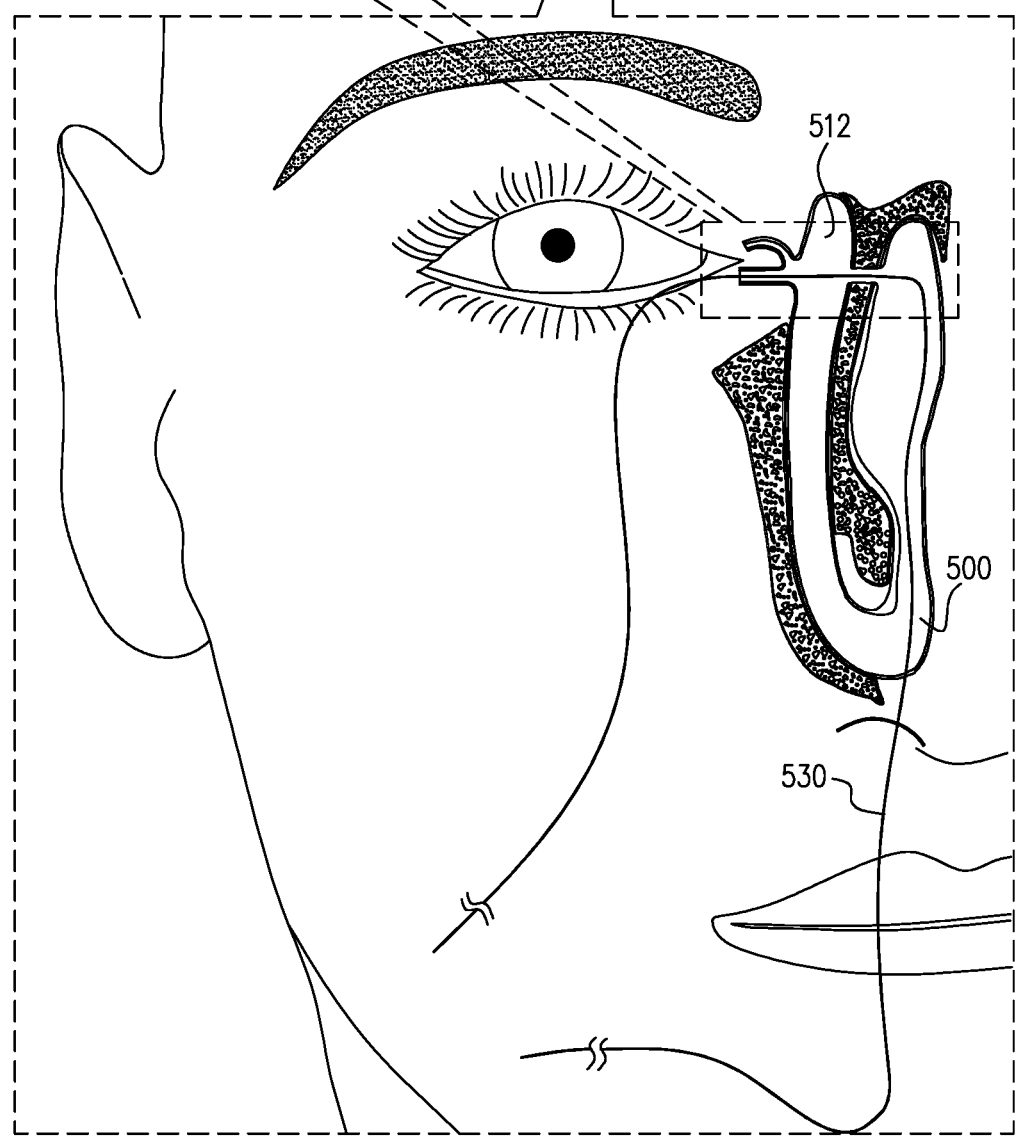

For some applications, as shown in FIG. 4F, at a dilation step 416, dilator 100 is advanced along and over guidewire 530 and through lacrimal passageway 510 and into bypass 520, and bypass 520 is dilated using dilator 100. As shown in FIG. 4G, dilator 100 is removed from the patient's body.

Figure 4H:
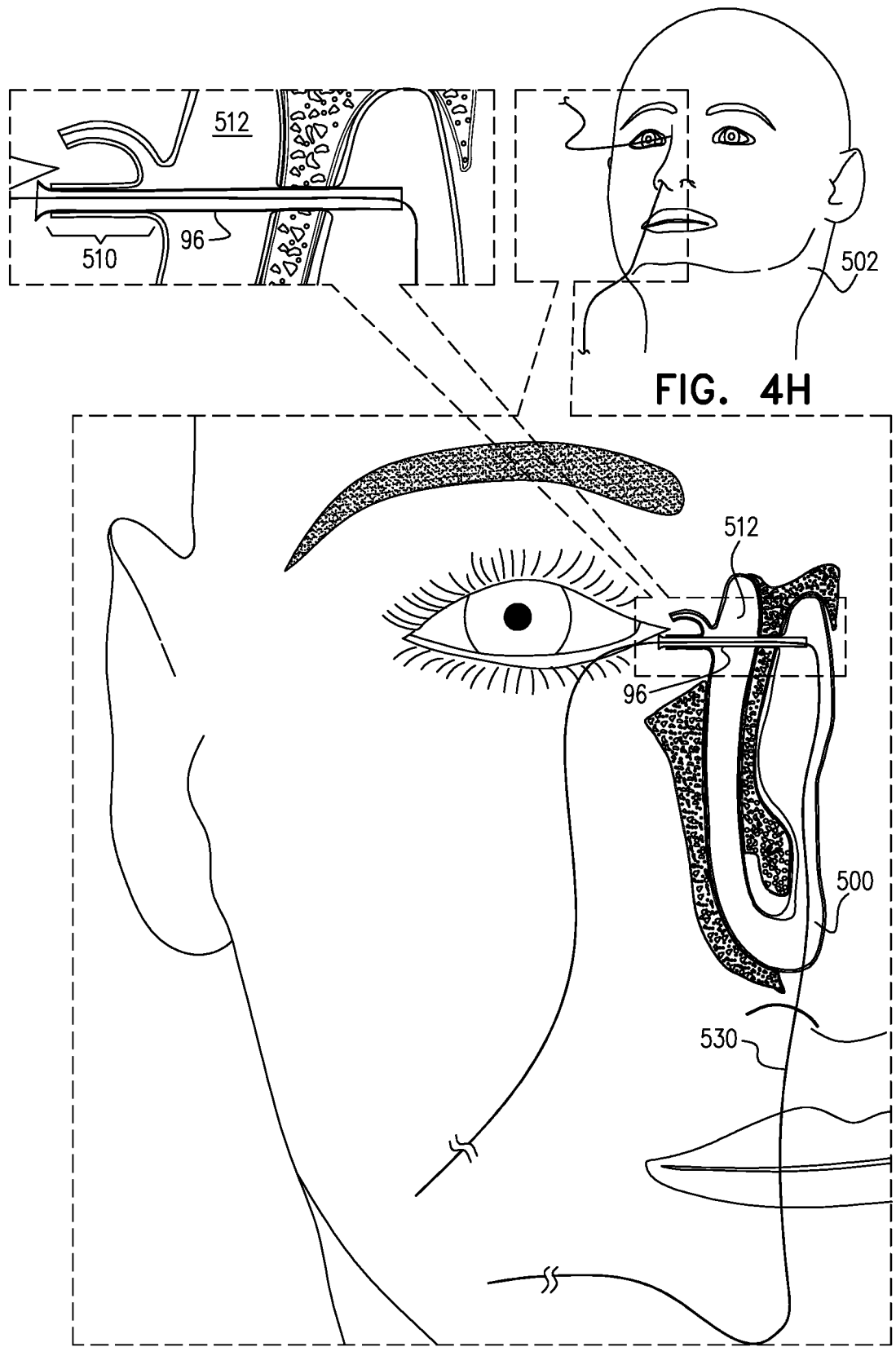
Figure 4I:
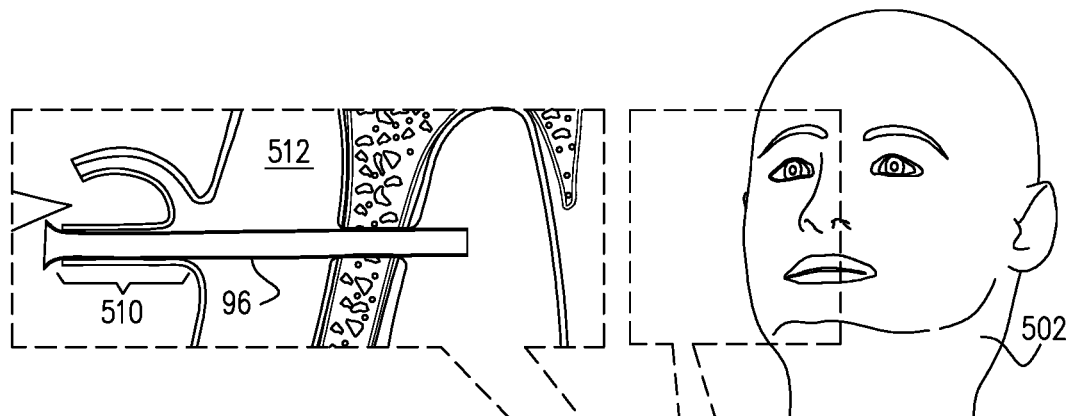
Figure 4I:
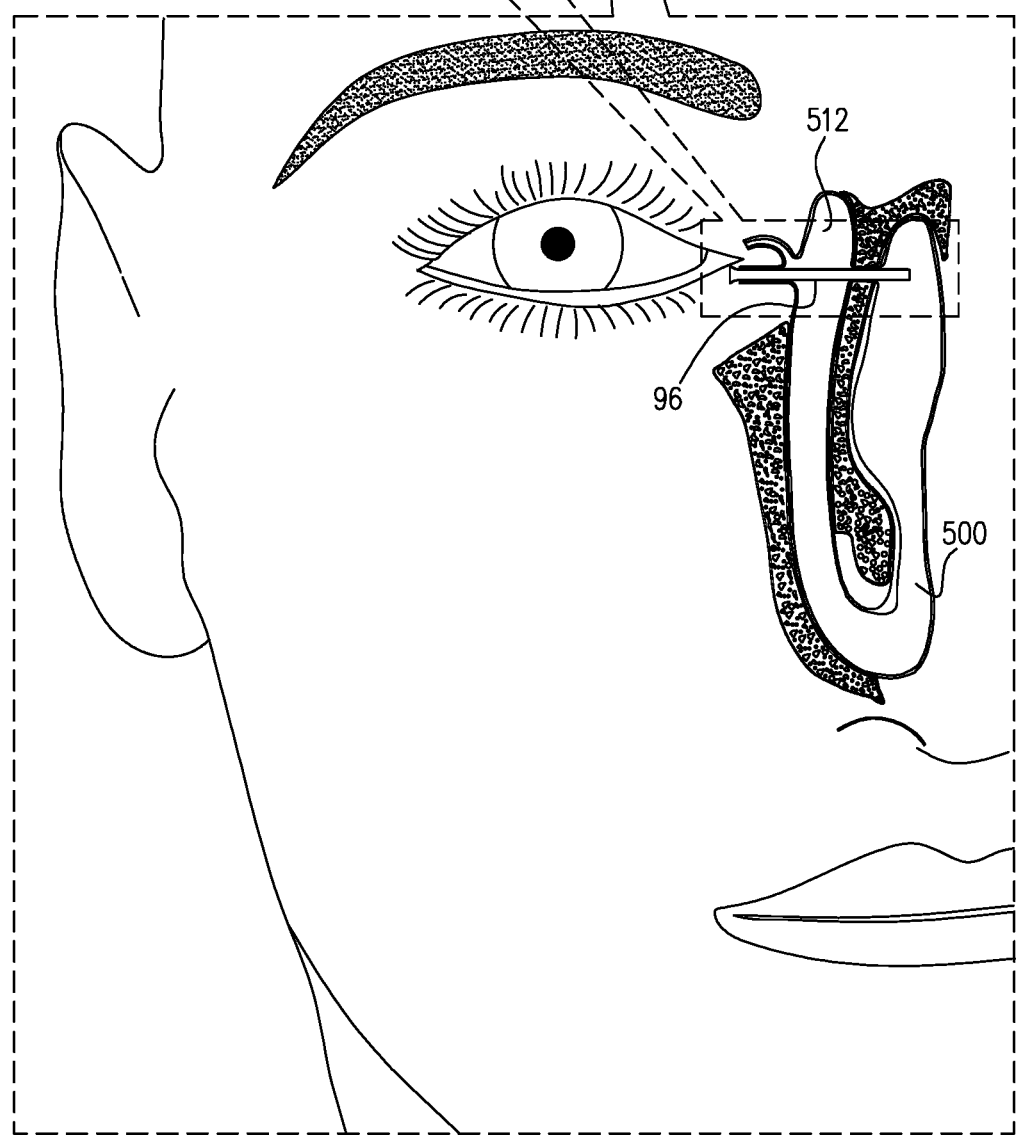

For some applications, such as shown in FIG. 4H, at a support step 418, tubular support element 96 is advanced along and over guidewire 530 and through lacrimal passageway 510 and into bypass 520, and guidewire 530 is removed from the patient's body while leaving the tubular support element in place in bypass 520, as shown in FIG. 4I. For example, tubular support element 96 may comprise a stent (e.g., comprising metal (e.g., Nitinol) and/or a polymer, e.g., silicone) or a polymer tube, e.g., comprising silicone. For some applications, tubular support element 96 is left in place long-term, while for other applications, tubular support element 96 is removed after patency of bypass 520 is achieved, such as after a few weeks. Although the proximal end of tubular support element 96 is shown as terminating outside lacrimal punctum 514, tubular support element 96 may alternatively be shorter, and terminate within lacrimal canal 516, common canaliculus 518, in lacrimal sac 512.

Reference is made to FIGS. 2B-C and FIG. 4B-E. For applications in which DCR tool 210, described hereinabove with reference to FIG. 2B, or DCR tool 310, described hereinabove with reference to FIG. 2C, is used to perform the DCR, guidewire placement step 408 does not comprise perforating shaft removal step 410; instead, perforating shaft 30 is left in lacrimal passageway 510 after forming bypass 520. At lacrimal guidewire insertion step 412, guidewire 530 is advanced through lacrimal guidewire-accepting channel 94 while perforating shaft 30 is disposed passing through lacrimal passageway 510, such that guidewire 530 passes through lacrimal passageway 510. Typically, guidewire 530 is advanced through lacrimal guidewire-accepting channel 94 while (a) perforating shaft 30 is disposed passing through lacrimal passageway 510 and bypass 520, and (b) distal perforating tip 32 is in contact with distal guide tip 42 of nasal guide component 40. Thereafter, lacrimal guide component 50, perforating shaft 30, and nasal guide component 40 are withdrawn from guidewire 530 and out of the patient's body, leaving guidewire 530 in place, as shown in FIG. 4E.

Reference is now made to FIGS. 5A-D, which are schematic illustrations of a locking mechanism 600 of nasal guide component 40, in accordance with an application of the present invention. In this configuration, as mentioned above with reference to FIG. 1, nasal guide component 40 comprises (a) outer guide element 80 that is shaped so as to define nasal-shaft-accepting channel 82 therethrough (labeled in FIG. 2A), and (b) nasal shaft 84 that is slidable through nasal-shaft-accepting channel 82, typically before nasal guide component 40 is inserted into the nasal cavity. Nasal shaft 84 is shaped so as to define distal guide tip 42 and nasal guidewire-accepting channel 70 (labeled in FIG. 2A). Providing nasal shaft 84 as a component separate from outer guide element 80 (and from the other elements of DCR guide 20) may enable reusability of DCR guide 20 with a plurality of disposable nasal shafts 84 (for example, because nasal shaft 84 may become slightly damaged, e.g., bent, during the surgical procedure).

Figure 5A:
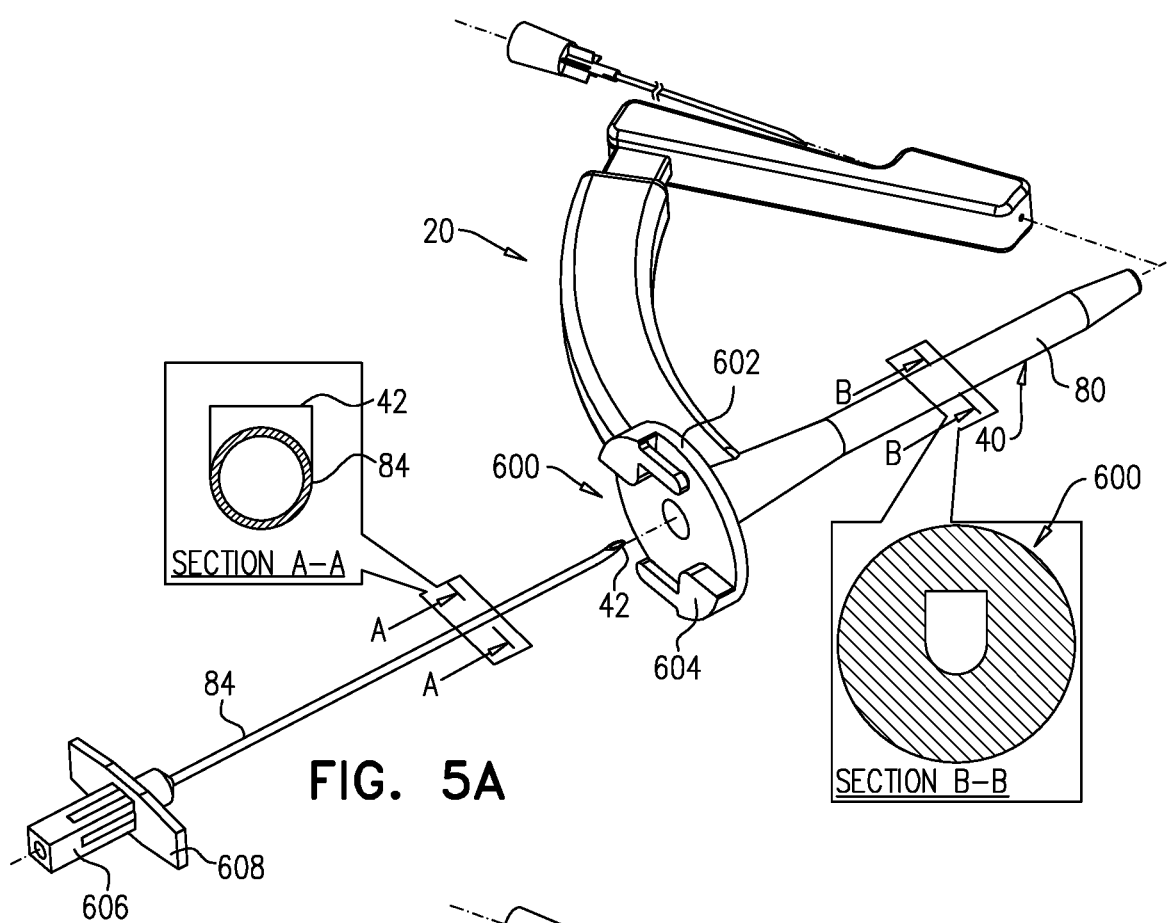
FIGS. 5A-D are schematic illustrations of a locking mechanism of a nasal guide component of the DCR tool of FIG. 1, in accordance with an application of the present invention.
Figure 5B:
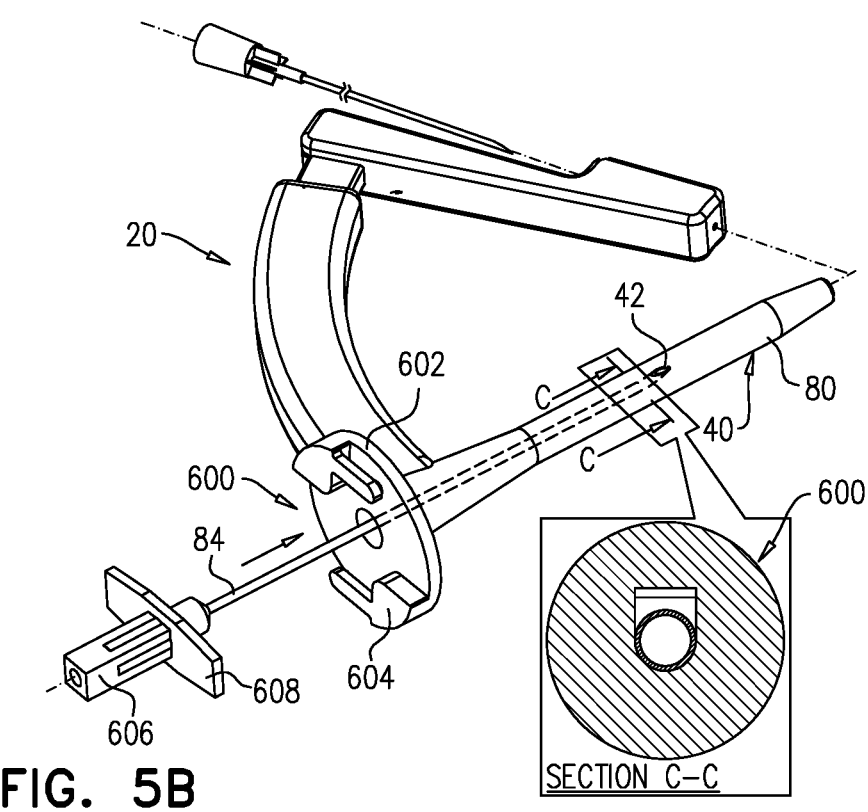
Figure 5C:
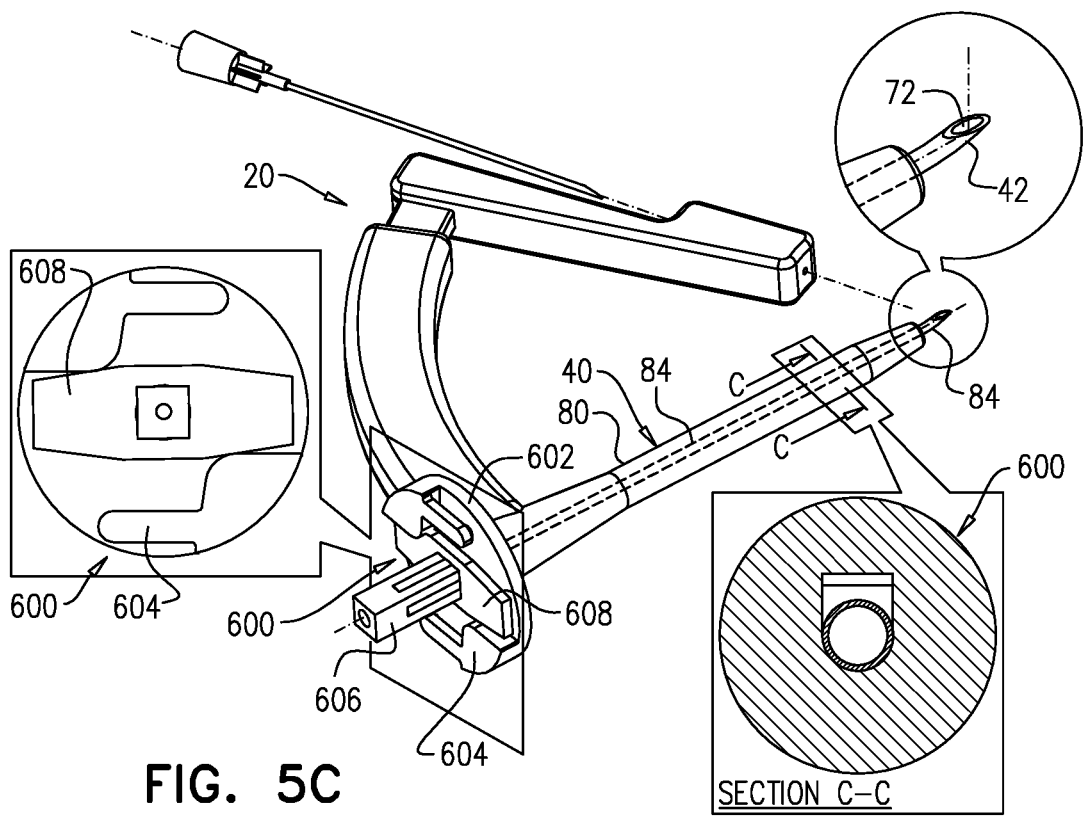
Figure 5D:
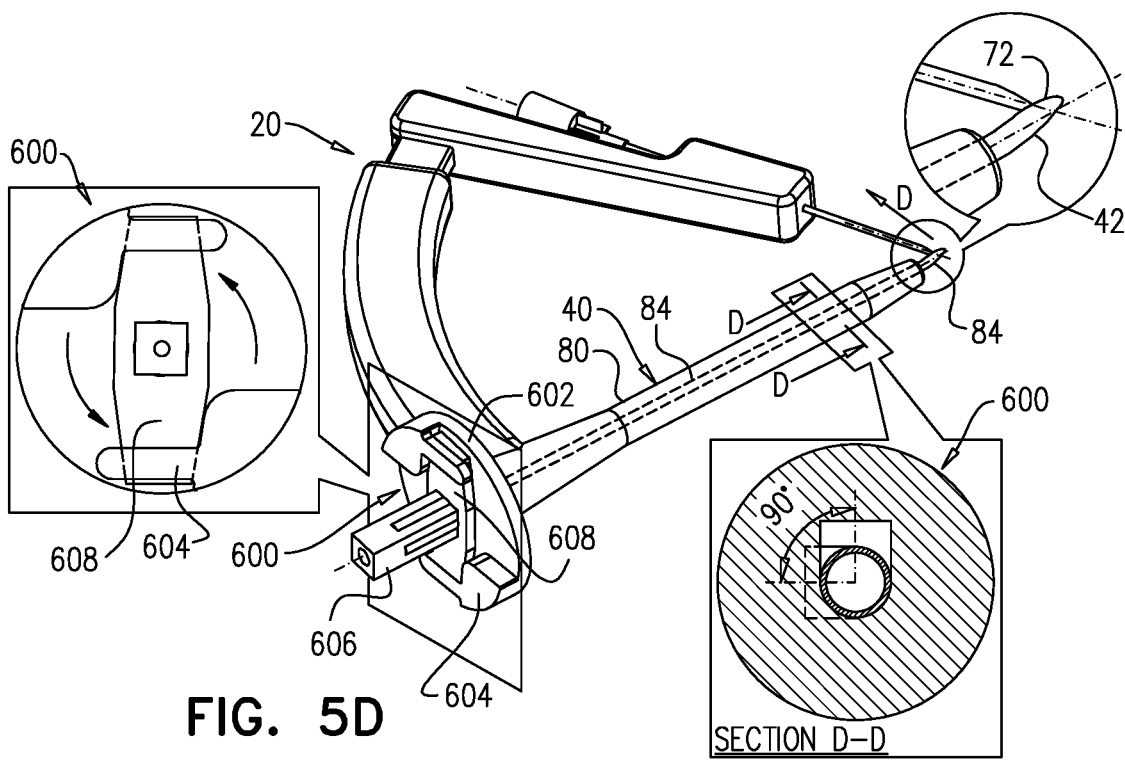

Typically, as shown in FIG. 5D, when outer guide element 80 and nasal shaft 84 are coupled together, distal opening 72 of nasal guidewire-accepting channel 70 is constrained by outer guide element 80 and nasal shaft 84 to face at least partially in lateral direction D, described hereinabove with reference to FIG. 1.

Optionally, but not necessarily, nasal guide component 40 comprises locking mechanism 600, which is configured to lock nasal shaft 84 rotationally with respect to nasal-shaft-accepting channel 82, thereby maintaining the rotational orientation of distal opening 72 of nasal guidewire-accepting channel 70, i.e., facing at least partially in lateral direction D after rotationally orienting distal guide tip 42, as shown in FIG. 5D. Locking mechanism 600 also typically locks nasal shaft 84 axially with respect to nasal-shaft-accepting channel 82, which fixes the axial position of distal guide tip 42 with respect to nasal guide component 40 and ensures that distal guide tip 42 falls in the path of advancement of distal tip 92 of lacrimal guidewire shaft 90, as described hereinabove with reference to FIG. 1.

FIG. 5A shows DCR guide 20 before insertion of nasal shaft 84 into nasal-shaft-accepting channel 82 (labeled in FIG. 2A) of outer guide element 80 of nasal guide component 40. FIG. 5B shows DCR guide 20 upon partial insertion of nasal shaft 84 into nasal-shaft-accepting channel 82. FIG. 5C shows DCR guide 20 after insertion of nasal shaft 84 into nasal-shaft-accepting channel 82, while locking mechanism 600 is in an unlocked state.

For some applications, as shown in FIG. 5D, rotation of nasal shaft 84 with respect to outer guide element 80 transitions locking mechanism 600 from the unlocked state to a locked state, in which distal opening 72 of nasal guidewire-accepting channel 70 is constrained and locked to face at least partially in lateral direction D. In addition, in the locked state, locking mechanism 600 locks nasal shaft 84 axially with respect to nasal-shaft-accepting channel 82.

For some applications, as shown in FIGS. 5A-D, nasal guide component 40 comprises a first proximal base 602 that is shaped so as to define a first coupling element 604 of locking mechanism 600, and nasal shaft 84 comprises a second proximal base 606 that is shaped so as to define a second coupling element 608 of locking mechanism 600. First and second coupling elements 604 and 608 are configured to be locked together, such as by rotation with respect to each other, as shown in FIG. 5D.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for performing dacryocystorhinostomy (DCR), the apparatus comprising a dacryocystorhinostomy (DCR) tool, which comprises:
   a perforating shaft having a distal perforating tip configured to form a bypass between a lacrimal sac and a nasal cavity through a lateral side of the lacrimal sac, a lacrimal bone, and nasal mucosa; and
   a DCR guide, which comprises:
      a nasal guide component, which is configured to be inserted into the nasal cavity and has a distal guide tip; and
      a lacrimal guide component, which is shaped so as to define a guide channel that is configured to orient the DCR guide with respect to the distal perforating tip of the perforating shaft during advancing of the distal perforating tip through a lacrimal passageway and into the lacrimal sac, until contact of the distal perforating tip with the distal guide tip of the nasal guide component blocks further advancing of the distal perforating tip, the lacrimal passageway including a lacrimal punctum, a lacrimal canal, and a common canaliculus,
   wherein the DCR guide is configured to constrain the distal guide tip of the nasal guide component to fall in a path of advancement of the distal perforating tip, and
   wherein the nasal guide component comprises (a) an outer guide element that is shaped so as to define a nasal-shaft-accepting channel therethrough, and (b) a nasal shaft that is slidable through the nasal-shaft-accepting channel, and wherein the nasal shaft is shaped so as to define the distal guide tip.

2. The apparatus according to claim 1, wherein the DCR guide is configured to set a desired angle between respective central longitudinal axes of the nasal guide component and the perforating shaft.

3. The apparatus according to claim 2, wherein the DCR guide is shaped so as to define an arcuate portion that is configured to allow relative movement between the nasal guide component and the lacrimal guide component to set the desired angle.

4. The apparatus according to claim 1, wherein the distal perforating tip is shaped as a drill bit.

5. The apparatus according claim 1, wherein the nasal guide component, including the distal guide tip, is shaped so as to define a nasal guidewire-accepting channel.

6. The apparatus according to claim 5, wherein a distal opening of the nasal guidewire-accepting channel faces at least partially in a lateral direction that faces toward the lacrimal guide component.

7. The apparatus according to claim 5,
   wherein the nasal shaft is shaped so as to define the distal guide tip and the nasal guidewire-accepting channel, and wherein when the outer guide element and the nasal shaft are coupled together, a distal opening of the nasal guidewire-accepting channel is constrained by the outer guide element and the nasal shaft to face at least partially in a lateral direction that faces toward the lacrimal guide component.

8. The apparatus according to claim 7, wherein the nasal guide component comprises a locking mechanism, which is configured to lock the nasal shaft rotationally with respect to the nasal-shaft-accepting channel, thereby maintaining the distal opening of the nasal guidewire-accepting channel facing at least partially in the lateral direction.

9. The apparatus according to claim 5, wherein the perforating shaft, including the distal perforating tip, is shaped so as to define a lacrimal guidewire-accepting channel.

10. The apparatus according to claim 5, wherein the DCR tool further comprises a lacrimal guidewire shaft having a distal tip, and wherein the lacrimal guidewire shaft, including the distal tip thereof, is shaped so as to define a lacrimal guidewire-accepting channel, wherein the guide channel of the lacrimal guide component is configured to orient the DCR guide with respect to the distal tip of the lacrimal guidewire shaft during advancing of the distal tip through the guide channel and the lacrimal passageway and into the lacrimal sac, and wherein the DCR guide is configured to constrain the distal guide tip of the nasal guide component to fall in a path of advancement of the distal tip of the lacrimal guidewire shaft.

11. The apparatus according to claim 5, wherein the DCR tool further comprises a dilator, which is configured to be advanced through the lacrimal passageway and into the bypass, and to dilate the bypass.

12. The apparatus according to claim 11, wherein the dilator comprises an inflatable element, which is configured to dilate the bypass by being inflated in the bypass.

13. The apparatus according to claim 11, further comprising a tubular support element, which is configured to be advanced through the lacrimal passageway and into the bypass, and to maintain patency of the bypass.

14. Apparatus for performing dacryocystorhinostomy (DCR), the apparatus for use with a guidewire and comprising a dacryocystorhinostomy (DCR) tool, which comprises:
   a lacrimal guidewire shaft, which is configured to be inserted into a lacrimal passageway and has a distal tip, wherein the lacrimal guidewire shaft, including the distal tip, is shaped so as to define a lacrimal guidewire-accepting channel, and wherein the lacrimal passageway includes a lacrimal punctum, a lacrimal canal, and a common canaliculus; and
   a DCR guide, which comprises:
      a nasal guide component, which is configured to be inserted into the nasal cavity and has a distal guide tip, wherein the nasal guide component, including the distal guide tip, is shaped so as to define a nasal guidewire-accepting channel; and
      a lacrimal guide component, which is shaped so as to define a guide channel that is configured to orient the DCR guide with respect to the distal tip of the lacrimal guidewire shaft during advancing of the distal tip through the lacrimal a passageway and into a lacrimal sac, until contact of the distal tip of the lacrimal guidewire shaft with the distal guide tip of the nasal guide component blocks further advancing of the distal tip of the lacrimal guidewire shaft, wherein the DCR guide is configured to constrain the distal guide tip of the nasal guide component to fall in a path of advancement of the distal tip of the lacrimal guidewire shaft, and wherein the nasal guide component comprises (a) an outer guide element that is shaped so as to define a nasal-shaft-accepting channel therethrough, and (b) a nasal shaft that is slidable through the nasal-shaft-accepting channel, and wherein the nasal shaft is shaped so as to define the distal guide tip.

15. The apparatus according to claim 14, wherein the DCR guide is configured to set a desired angle between respective central longitudinal axes of the nasal guide component and the lacrimal guidewire shaft.

16. The apparatus according to claim 15, wherein the DCR guide is shaped so as to define an arcuate portion that is configured to allow relative movement between the nasal guide component and the lacrimal guide component to set the desired angle.

17. The apparatus according to claim 14, wherein a distal opening of the nasal guidewire-accepting channel faces at least partially in a lateral direction that faces toward the lacrimal guide component.

18. The apparatus according to claim 14, wherein when the outer guide element and the nasal shaft are coupled together, a distal opening of the nasal guidewire-accepting channel is constrained by the outer guide element and the nasal shaft to faces at least partially in a lateral direction that faces toward the lacrimal guide component.

19. The apparatus according to claim 18, wherein the nasal guide component comprises a locking mechanism, which is configured to lock the nasal shaft rotationally with respect to the nasal-shaft-accepting channel, thereby maintaining the distal opening of the nasal guidewire-accepting channel facing at least partially in the lateral direction.

* * * * *